United States Patent
Shiau et al.

(10) Patent No.: US 9,394,261 B2
(45) Date of Patent: Jul. 19, 2016

(54) ARYL AMINE SUBSTITUTED PYRIMIDINE AND QUINAZOLINE AND THEIR USE AS ANTICANCER DRUGS

(71) Applicants: National Yang-Ming University, Taipei (TW); National Taiwan University, Taipei (TW)

(72) Inventors: Chung-Wai Shiau, Taipei (TW); Kuen-Feng Chen, Taipei (TW)

(73) Assignees: NATIONAL YANG-MING UNIVERSITY, Taipei (TW); NATIONAL TAIWAN UNIVERSITY, Taipei (TW)

(*) Notice: Subject to any disclaimer, the term of this patent is extended or adjusted under 35 U.S.C. 154(b) by 0 days.

(21) Appl. No.: 14/631,248

(22) Filed: Feb. 25, 2015

(65) Prior Publication Data

US 2015/0246891 A1    Sep. 3, 2015

Related U.S. Application Data

(63) Continuation-in-part of application No. 14/026,545, filed on Sep. 13, 2013, now abandoned.

(60) Provisional application No. 61/700,923, filed on Sep. 14, 2012.

(51) Int. Cl.
| | |
|---|---|
| A61K 31/517 | (2006.01) |
| C07D 239/95 | (2006.01) |
| C07D 239/94 | (2006.01) |
| C07D 239/42 | (2006.01) |
| C07D 239/48 | (2006.01) |

(52) U.S. Cl.
CPC ............ *C07D 239/95* (2013.01); *C07D 239/42* (2013.01); *C07D 239/48* (2013.01); *C07D 239/94* (2013.01)

(58) Field of Classification Search
CPC .. C07D 239/95; C07D 239/42; C07D 239/48; C07D 239/94
See application file for complete search history.

(56) References Cited

U.S. PATENT DOCUMENTS

| 7,790,884 B2 | 9/2010 | Kontani et al. | |
| 2014/0080848 A1* | 3/2014 | Shiau ................... | C07D 239/42 514/266.4 |

FOREIGN PATENT DOCUMENTS

| WO | WO 95/21613 A1 | 8/1995 |
| WO | WO 2004/013091 A2 | 2/2004 |
| WO | WO 2005/082865 A1 | 9/2005 |
| WO | WO 2005/123697 A1 | 12/2005 |

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*
Tseng, et al., "CIP2A is a target of bortezomib in human triple negative breast cancer cells", Breast Cancer Research, 2012, pp. 1-14.
Chen, et al., "Development of erlotinib derivatives as CIP2A-ablating agents independent of EGFR activity", Bioorganic & Medicinal Chemistry 20, 2012, pp. 6144-6153.
Liu, et al., "Cancerous inhibitor of protein phosphatase 2A determines bortezomib-induced apoptosis in leukemia cells", Molecular & Cellular Basis of Leukemia & Lymphoma, 2013. pp. 729-738.
Yu, et al., "Inhibition of CIP2A determines erlotinib-induced apoptosis in hepatocelllular carcinoma", Biochemical Pharmacology 85, 2013, pp. 356-366.
Huang, et al., "Bortezomib ehances radiation-induced apoptosis in solid tumors by inhibiting CIP2A", Cancer Letters 317, 2012, pp. 9-15.
Junttila, et al., "CIP2A Inhibits PP2A in Human Malignancies", Cell 130, 2007, pp. 51-62.
Choi, et al., "Increase in CIP2A expression is aassociated with doxorubicin resistance", FEBS Letters 585, 2011, pp. 755-760.
Khanna, et al., "MYC-Dependent Regulation and Prognostic Role of CIP2A in Gastric Cancer", Journal of National Cancer Institute, 2009; 101, pp. 793-805.
Chen, et al., "Molecular Cancer Therapeutics", Mol. Cancer Ther. 2011; 10, pp. 892-901, Published Online First Mar. 10, 2011.
Ma, et al., "Overexpression and Small Molecule-Triggered Downregulation of CIP2A in Lung Cancer", Plos One, May 2011, vol. 6, Issue 5, pp. 1-10.
A. Gazit et al., 4 Bioorganic & Medicinal Chemistry, 1203-1207 (1996).
K-F Chen et al., 20 Bioorganic & Medicinal Chemistry, 6144-6153 (2012).
K. Abouzid et al., 16 Bioorganic & Medicinal Chemistry, 7543-7551 (2008).
K. Yokoyama et al., 16 Bioorganic & Medicinal Chemistry, 7968-7974 (2008).

* cited by examiner

*Primary Examiner* — Alexander R Pagano
(74) *Attorney, Agent, or Firm* — Muncy, Geissler, Olds & Lowe, P.C.

(57) ABSTRACT

A series of mono- and di-substituted quinazoline and pyrimidine derivatives based on the skeleton of erlotinib (an EGFR inhibitor) were synthesized and their bioactivities against hepatocellular carcinoma and human lung adenocarcinoma were evaluated.

13 Claims, 13 Drawing Sheets

Erlotinib $IC_{50}=1.36\mu M$

ARYL AMINE SUBSTITUTED PYRIMIDINE AND QUINAZOLINE AND THEIR USE AS ANTICANCER DRUGS

CROSS REFERENCE TO RELATED APPLICATIONS

This application is a Continuation-in-Part of co-pending application Ser. No. 14/026,545, filed on 13 Sep. 2013, for which priority is claimed under 35 U.S.C. §120; and this application claims priority of U.S. Provisional Application No. 61/700,923 filed on 14 Sep. 2012 under 35 U.S.C. §119 (e), the entire contents of all of which are hereby incorporated by reference.

BACKGROUND

1. Technical Field

The disclosure relates to pyrimidine and quinazoline derivatives and their use as anticancer drugs.

2. Description of Related Art

Overexpression of cancerous inhibitor of protein phosphatase 2A (abbreviated as CIP2A) has been found in several common human cancers including acute leukemia, prostate cancer, non-small cell lung cancer, gastric cancer, head and neck cancer, colon cancer and breast cancer and has been linked to clinical aggressiveness in tumors and promotion of the malignant growth of cancer cells. CIP2A interacts directly with the transcription factor c-Myc and inhibits the PP2A dephosphorylation of c-Myc, thereby stabilizing the oncogenic c-Myc from degradation.

Protein phosphatase 2A (abbreviated as PP2A) is a crucial regulator of cell proliferation by dephosphorylation of protein kinases on serine or threonine residues. PP2A is composed of three subunits which regulate substrate specificity, cellular localization and enzymatic activity. For example, PP2A dephosphorylates p-Akt at serine 473 and reduces the cell growth. Hence, the CIP2A-PP2A-Akt signaling cascade is thought to be an important survival regulator in cancers. Accordingly, downregulation of c-Myc and p-Akt by CIP2A ablation is a promising anticancer strategy.

Some compounds have been found to be capable of repressing repress CIP2A expression and subsequently reducing p-Akt level and induce apoptosis in hepatocellular carcinoma (HCC). For example, the above phenomenon had been observed for bortezomib, a proteasome inhibitor.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present invention is directed to an aryl amine substituted pyrimidine having a chemical structure (I) or (II) below:

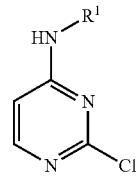

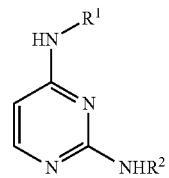

The $R^1$ and $R^2$ above are same or different substituted phenyl groups, and the substituted phenyl group each is

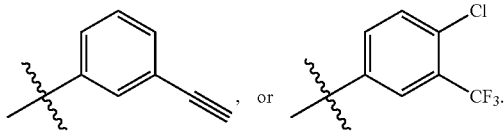

In another aspect, the present invention is directed to an aryl amine substituted quinazoline having a chemical structure (III) or (IV) below:

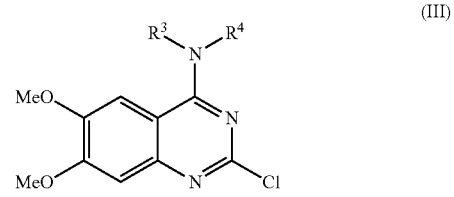

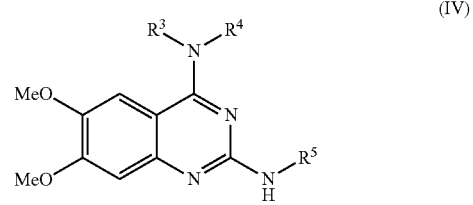

The $R^3$ above is an aliphatic-substituted phenyl group, a halo-substituted phenyl group, a hydroxyl-substituted phenyl group, or an aryloxy-substituted phenyl group. The $R^4$ above is H, an aliphatic group with carbon number of 1-5, an amino-substituted aliphatic group, or a benzyl group. The $R^5$ above aliphatic substituted phenyl group, a halo-substituted phenyl group, an aryloxy-substituted phenyl group, a benzyl group, a halo substituted benzyl group, an alkoxy substituted phenyl group, an arylamino-substituted phenyl group, an amidyl-substituted phenyl group, an ArO(CO)NH-substituted phenyl group, or Ph-SO$_2$—NH-substituted phenyl group, with the proviso that when $R^3$ is

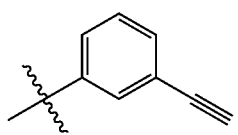 [SMILES: *c1cccc(C#C)c1]
and R⁴ is H, the R⁵ does not include
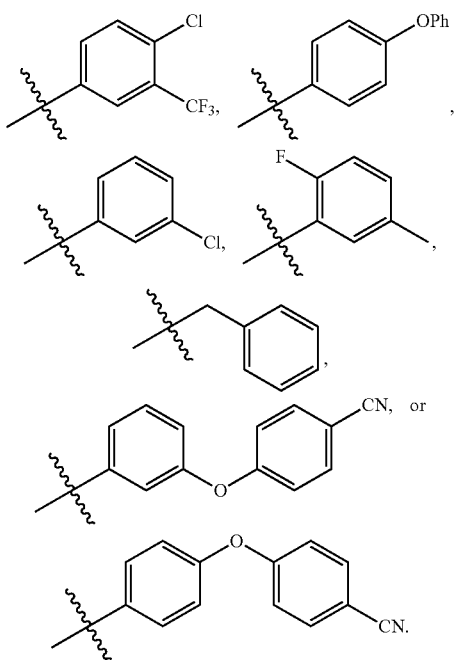
According to an embodiment, the R³ is
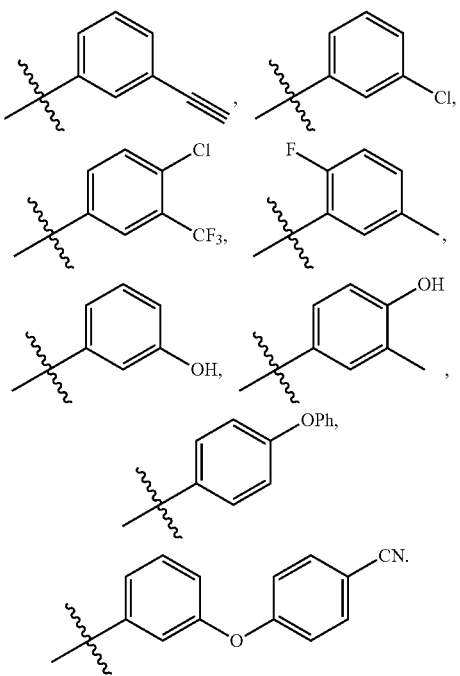
According to another embodiment, the R⁴ is H, Me
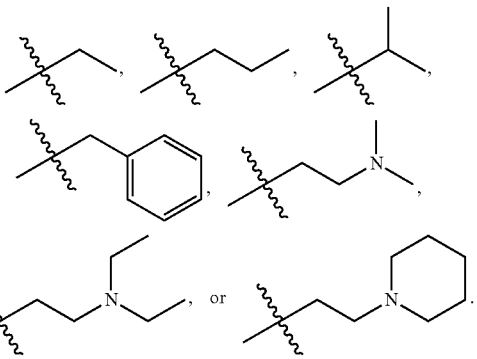
According to yet another embodiment, the R⁵ is
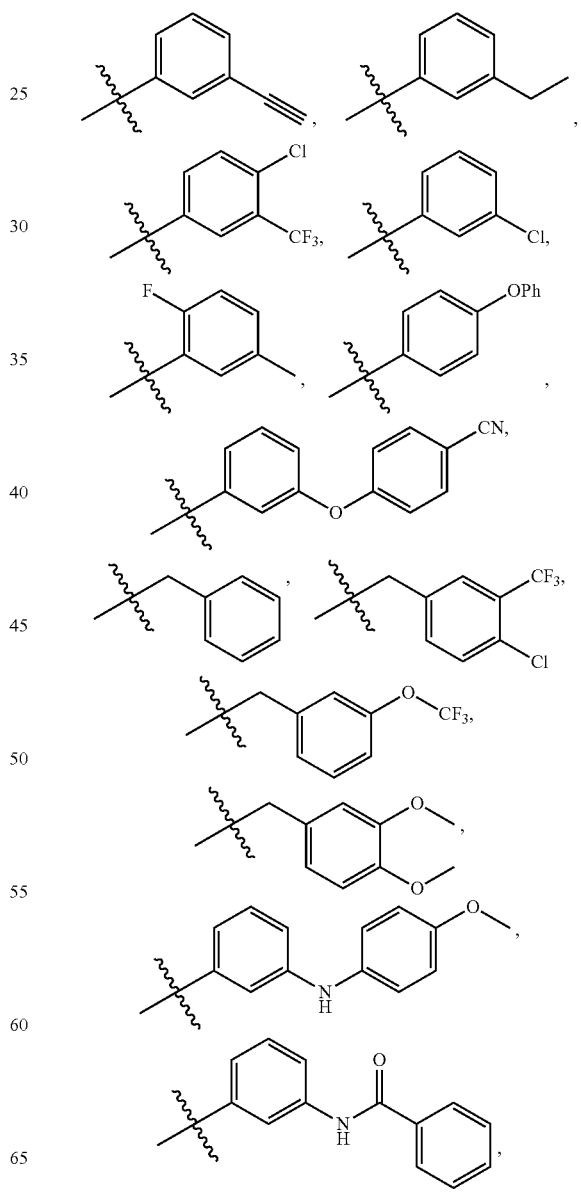

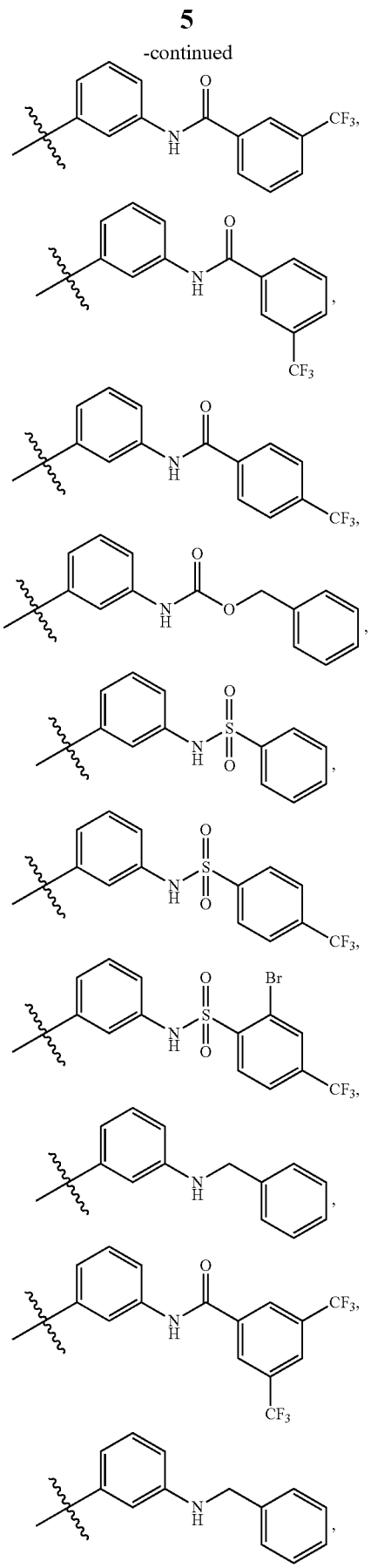
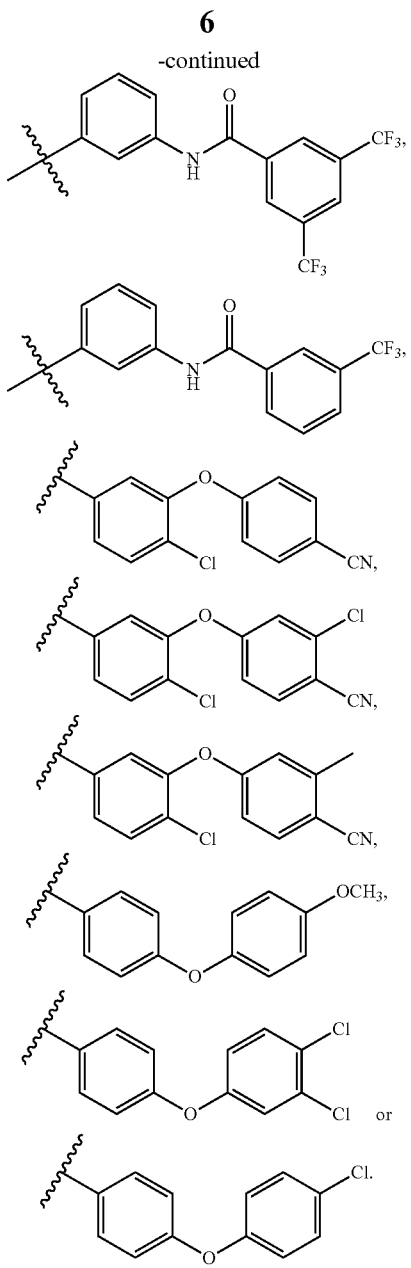
In yet another aspect, the present invention directs to a pharmaceutical composition. The pharmaceutical composition comprises an effective amount of a compound having a chemical structure (VII) below and a pharmaceutically acceptable carrier.
The $R^5$ above is
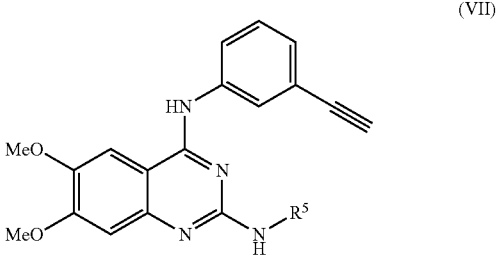

In yet another aspect, the present invention directs to a method of inhibiting the expression of cancerous inhibitor of PP2A. The method comprises contacting a cell with an effective amount of a compound having a chemical structure (VII) above. The $R^5$ above is -continued

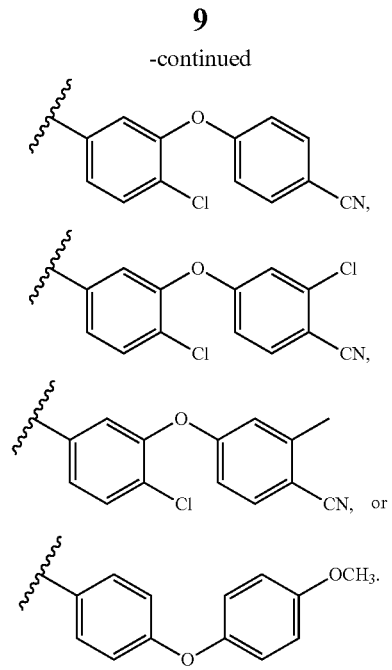

In yet another aspect, the present invention directs to a method of treating cancer. The method comprises administrating an effective amount of a compound having a chemical structure (VII) above by a needed subject. The $R^5$ above is

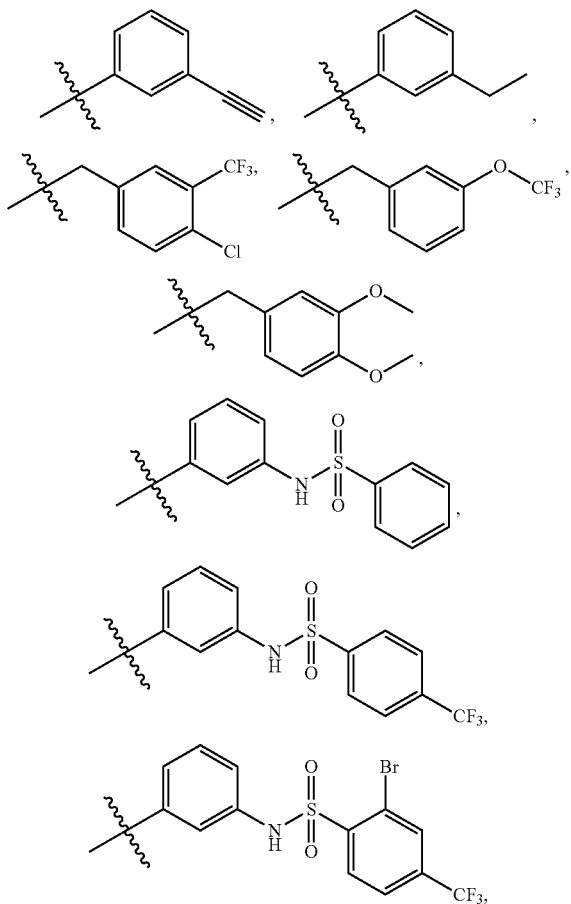

-continued

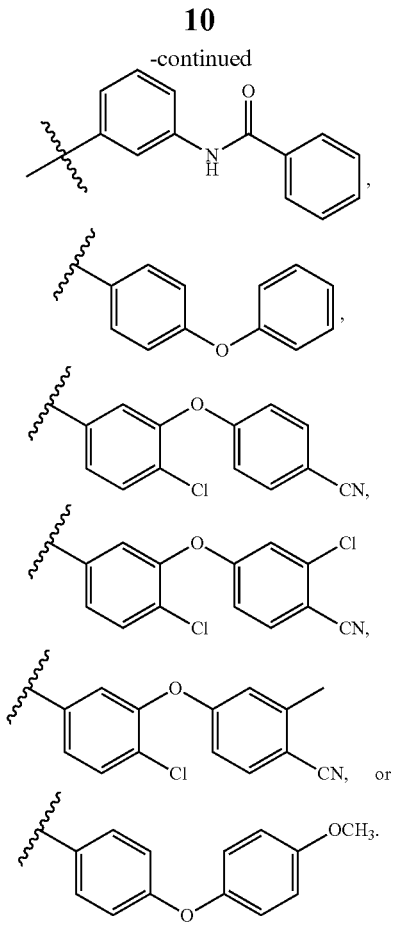

Many of the attendant features will be more readily appreciated as the same becomes better understood by reference to the following detailed description considered in connection with the accompanying drawings.

DETAILED DESCRIPTION

Figure 1A:
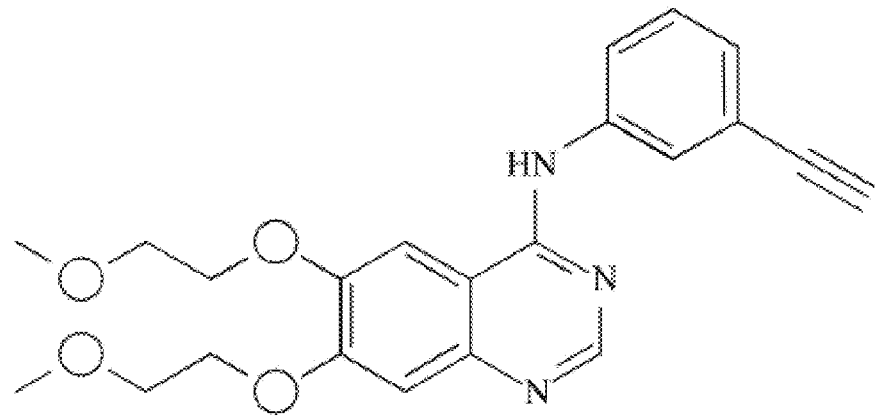
FIGS. 1A-1B are the western blot analysis of inhibiting EGFR phosphorylation activity by erlotinib and compound 8 in PC9 cells (a human lung adenocarcinoma), respectively.
Figure 1A:
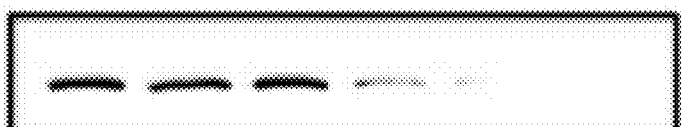
Figure 1A:
Figure 1A:
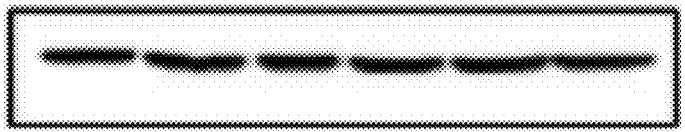

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The following abbreviations are used: CDCl$_3$, deuterated chloroform; DMSO-d6, dimethyl sulfoxide-d6; i-PrOH, isopropyl alcohol; EtOAc, ethyl acetate; DMF, N,N-dimethylformamide; MeOH, methanol; THF, tetrahydrofuran; EtOH, ethanol; DMSO, dimethyl sulfoxide; DIPEA, diisopropylethylamine; DCM, dichloromethane.

Synthesis of Pyrimidine Derivatives

Synthesis Scheme I

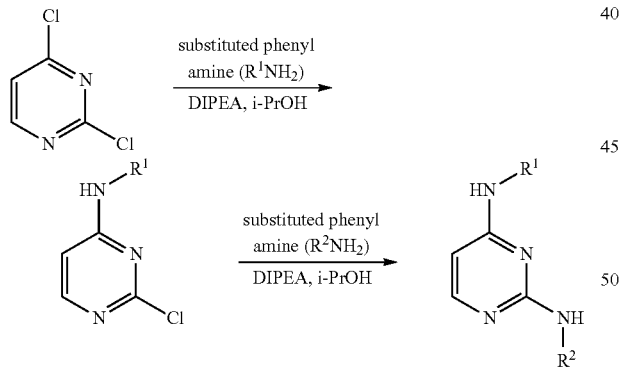

In the synthesis scheme I above, R$^1$ and R$^2$ can be the same or different substituted phenyl group, such as a mono-substituted phenyl group or a di-substituted phenyl group. The mono-substituted phenyl group can be

-continued

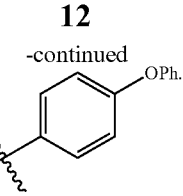

The di-substituted phenyl group can be

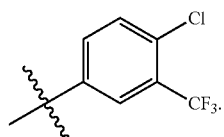

One or both of the R$^1$ and R$^2$ also can be a benzyl group,

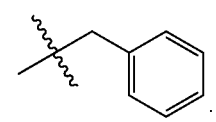

The general synthesis procedure of the pyrimidine derivatives is described as follow.

A solution of 2,4-dichloropyrimidine (1.0 mmol) and N,N-diisopropylethylamine (DIPEA) (100 μl) in isopropyl alcohol was added with 0.7 mmol of a substituted phenyl amine, and the mixtures was stirred in ice-bath for 30 minutes. The resulting mixture was stirred at room temperature for 8 hours. After the reaction was completed, the reaction mixture was washed with water, extracted with EtOAc, and the organic layer was dried over MgSO$_4$. After removal of MgSO$_4$ by filtration and evaporation of solvents, the crude residue was purified by chromatography on a silica gel column (silica gel columns 60, 0.063-0.200 mm or 0.040-0.063 mm, Merck; basic silica gel) using MeOH/CH$_2$Cl$_2$ as eluent (0% to 2%) to give compounds 1-7 (yield: 3-27%) below.

Embodiment 1

Synthesis of Mono-Substituted Pyrimidine Derivatives

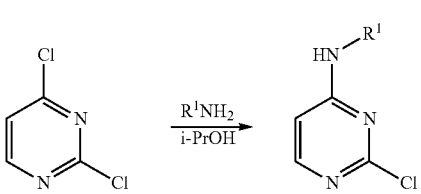

| Compound No | R$^1$ |
|---|---|
| 1 | 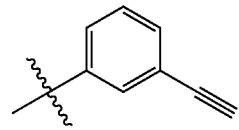 [SMILES: *c1cccc(C#C)c1] |

| Compound No | R¹ |
|---|---|
| 2 | 3-chlorophenyl |
| 3 | 4-chloro-3-(trifluoromethyl)phenyl |
| 4 | 4-phenoxyphenyl |
| 5 | benzyl |

The spectral data of the above compounds are listed below.

Compound 1: 2-Chloro-N-(3-ethynylphenyl)pyrimidin-4-amine

¹H NMR (400 MHz, MeOH-$d_4$): δ 3.48 (s, 1H), 6.66 (d, J=6.0 Hz, 1H), 7.18 (d, J=7.6 Hz, 1H), 7.30 (t, J=7.6 Hz, 1H), 7.61 (d, J=8.4 Hz, 1H), 7.72 (s, 1H), 8.05 (d, J=6.0 Hz, 1H); ¹³C NMR (100 MHz, CDCl₃): δ 78.6, 82.8, 102.9, 123.7, 123.9, 126.5, 129.8, 130.0, 137.5, 158.5, 161.1, 162.6; HRMS calculated for $C_{12}H_8ClN_3$ (M+H): 230.0485. Found: 230.0478. Yield: 5%.

Compound 2: 2-Chloro-N-(3-chlorophenyl)pyrimidin-4-amine

¹H NMR (400 MHz, CDCl₃): δ 6.59 (d, J=5.6 Hz, 1H), 7.18 (d, J=8.0 Hz, 1H), 7.22 (d, J=8.4 Hz, 1H), 7.31 (t, J=8.0 Hz, 1H), 7.36 (s, 1H), 8.15 (d, J=5.6 Hz, 1H); ¹³C NMR (100 MHz, CDCl₃): δ 102.9, 120.6, 122.6, 125.8, 130.6, 135.2, 138.4, 158.2, 160.8, 162.0; HRMS calculated for $C_{10}H_7Cl_2N_3$ (M+H): 240.0095. Found: 240.0101. Yield: 6%.

Compound 3: 2-Chloro-N-(4-chloro-3-(trifluoromethyl)phenyl)pyrimidin-4-amine ¹H NMR (400 MHz, CDCl₃): δ 6.55 (d, J=5.6 Hz, 1H), 7.11 (s, 1H), 7.51 (d, J=8.4 Hz, 1H), 7.63 (d, J=8.4 Hz, 1H), 7.72 (s, 1H), 8.20 (d, J=5.6 Hz, 1H); ¹³C NMR (100 MHz, CDCl₃): δ 103.6, 120.8 (q), 123.7, 125.8, 128.1, 129.2, 129.5, 132.5, 136.2, 158.3, 160.9, 161.4; HRMS calculated for $C_{11}H_6Cl_2F_3N_3$ (M+H): 307.9969. Found: 307.9969. Yield: 3%.

Compound 4: 2-Chloro-N-(4-phenoxyphenyl)pyrimidin-4-amine

¹H NMR (400 MHz, MeOH-$d_4$): δ 6.63 (d, J=6.0 Hz, 1H), 6.96-7.00 (m, 4H), 7.08 (t, J=7.2 Hz, 1H), 7.33 (t, J=8.0 Hz, 2H), 7.54 (d, J=8.0 Hz, 2H), 8.01 (d, J=6.0 Hz, 1H); ¹³C NMR (100 MHz, CDCl₃): δ 102.1, 119.0, 119.6, 123.7, 125.5, 129.8, 131.7, 155.6, 156.7, 158.0, 160.8, 163.0; HRMS calculated for $C_{16}H_{12}ClN_3O$ (M−H): 296.0591. Found: 296.0583. Yield: 14%.

Compound 5: N-Benzyl-2-chloropyrimidin-4-amine

¹H NMR (400 MHz, MeOH-$d_4$): δ 4.55 (s, 2H), 6.60 (d, J=5.2 Hz, 1H), 7.19-7.22 (m, 1H), 7.26-7.31 (m, 4H), 8.12 (d, J=5.2 Hz, 1H); ¹³C NMR (100 MHz, MeOH-$d_4$): δ 43.8, 104.4, 126.9, 127.4, 128.2, 138.3, 154.3, 160.2, 163.7; HRMS calculated for $C_{11}H_{10}ClN_3$ (M+H): 220.0642. Found: 220.0640. Yield: 27%.

Embodiment 2

Synthesis of Di-Substituted Pyrimidine Derivatives

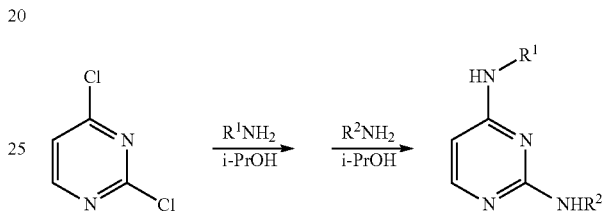

| Compound No | R¹ | R² |
|---|---|---|
| 6 | 3-ethynylphenyl | 3-ethynylphenyl |
| 7 | 4-chloro-3-(trifluoromethyl)phenyl | 4-chloro-3-(trifluoromethyl)phenyl |

The spectral data of the above compounds are listed below.

Compound 6: N²,N⁴-Bis(3-ethynylphenyl)pyrimidine-2,4-diamine

¹H NMR (400 MHz, CDCl₃): δ 3.04 (s, 1H), 3.10 (s, 1H), 6.16 (d, J=6.0 Hz, 1H), 7.13 (d, J=8.0 Hz, 1H), 7.19-7.31 (m, 4H), 7.37 (d, J=8.0 Hz, 1H), 7.45 (s, 1H), 7.54 (d, J=8.4 Hz, 1H), 7.72 (s, 1H), 7.92 (brs, 1H), 8.06 (d, J=6.0 Hz, 1H); ¹³C NMR (100 MHz, CDCl₃): δ 77.0, 77.8, 83.0, 83.8, 97.2, 120.5, 122.4, 122.6, 123.0, 123.1, 125.2, 126.1, 128.0, 128.8, 129.3, 138.5, 139.7, 157.2, 159.8, 161.0; HRMS calculated for $C_{20}H_{14}N_4$ (M+H): 311.1297. Found: 311.1291. Yield: 10%.

Compound 7: N²,N⁴-Bis(4-chloro-3-(trifluoromethyl)phenyl)pyrimidine-2,4-diamine ¹H NMR (400 MHz, CDCl₃): δ 6.16 (d, J=5.6 Hz, 1H), 6.60 (s, 1H), 7.10 (s, 1H), 7.38 (d, J=8.4 Hz, 1H), 7.45 (d, J=8.0 Hz, 1H), 7.60 (d, J=8.4 Hz, 1H), 7.68 (d, J=8.8 Hz, 1H), 7.72 (s, 1H), 7.92 (s, 1H), 8.12 (d, J=5.6 Hz, 1H); $^{13}$C NMR (100 MHz, MeOH-d$_4$): δ 99.6, 118.0 (q), 118.4 (q), 118.7, 118.9, 121.4, 121.6, 123.0, 123.3, 123.9, 124.1, 124.2, 124.3, 126.91-128.30 (m), 131.2, 131.4, 139.0, 139.6, 155.8, 159.1, 160.6; HRMS calculated for $C_{18}H_{10}Cl_2F_6N_4$ (M+H): 467.0265. Found: 467.0254. Yield: 5%.

Synthesis of Quinazoline Derivatives

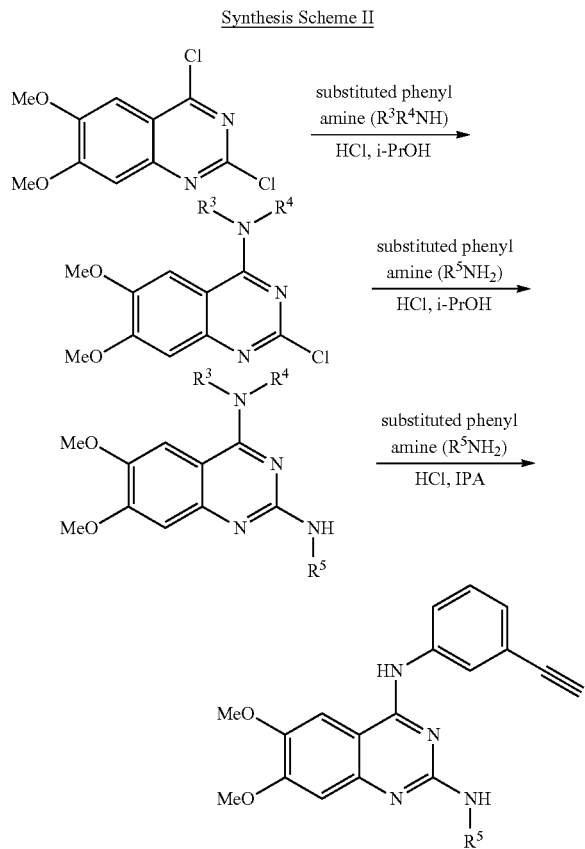

In the synthesis scheme II, $R^3$ and $R^5$ can be the same or different substituted phenyl groups, such as a mono-substituted phenyl group or a di-substituted phenyl group. The mono-substituted phenyl group can be

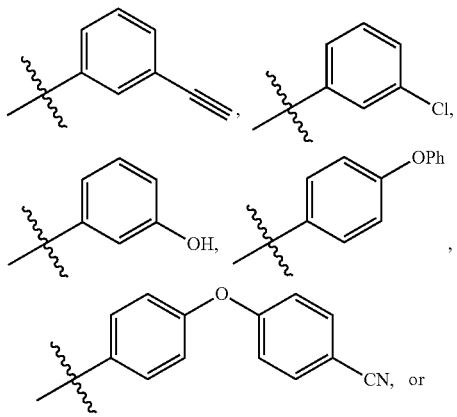

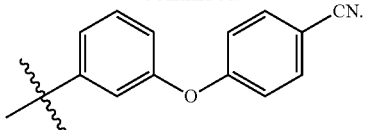

The di-substituted phenyl group can be

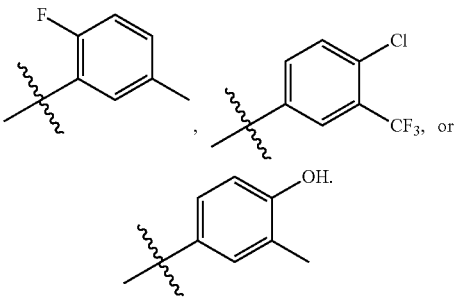

One or both of $R^3$ and $R^5$ also can be a benzyl group,

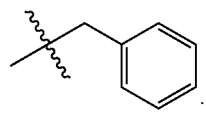 [SMILES: *Cc1ccccc1]

$R^4$ can be H or methyl group.

A series of quinazoline derivatives were designed and synthesized by the general procedure illustrated in scheme II above. Based on the core quinazoline structure of these quinazoline derivatives, a commercially available dichloroquinazoline was chosen as a starting material. A series of mono-quinazoline derivatives (compounds 8-17) were generated with various substituted phenylamines by replacement of the chloride in the quinazoline (Embodiment 3). Then, the other chloride from the mono-substitute quinazolines was replaced with various substituted phenylamines to yield compounds 18-24 (Embodiment 4).

Embodiment 3

Synthesis of Mono-Substituted Quinazoline Derivatives

The general synthesis procedure of the mono-substituted quinazoline derivatives are stated as follow. Substituted phenyl amine (0.8 mmol) was added to a solution of 2,4-dichloro-6,7-dimethoxyquinazoline (1.0 mmol) in isopropyl alcohol (5 ml), followed by the addition of a drop of concentrated HCl (100 µl). The resulting mixture was stirred at 60° C. for 2 hours. The mixture was filtered, and the solid was washed with isopropyl alcohol then dried under vacuum to give compounds 8, and 10-17. This procedure afforded the expected coupling product as a white or yellow solid (yield: 21%-95%).

Compound 9 was synthesized from compound 8, and the further synthesis procedure is as follow. Methyl iodide (56 µl, 0.90 mmol) was added to a solution of compound 8 (61.0 mg, 0.18 mmol) and sodium hydride (60% oil suspension, 8.63 mg, 0.36 mmol) in 2 ml of DMF cooled to 0° C. The mixture was stirred at 0° C. for 1 hour, then allowed to warm to room temperature and stirred for another 1 hour. The reaction mixture was washed with water, and then extracted with EtOAc. The organic phase was dried over MgSO$_4$, filtered and concentrated under reduced pressure. The crude residue was purified by chromatography on a silica gel column (silica gel columns 60, 0.063-0.200 mm or 0.040-0.063 mm, Merck; basic silica gel) using EtOAc/hexane as eluent (0% to 40%) to give compound 9.

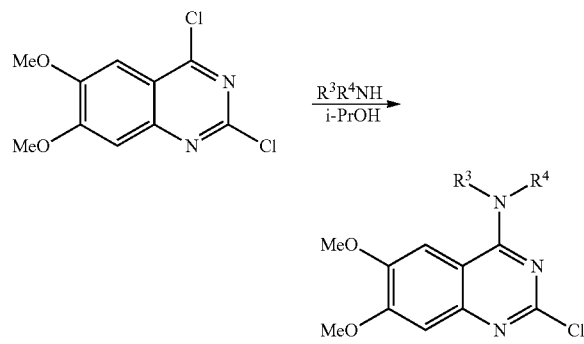

| Compound No | R$^3$ | R$^4$ |
|---|---|---|
| 8 | 3-ethynylphenyl | H |
| 9 | 3-ethynylphenyl | Me |
| 10 | 3-chlorophenyl | H |
| 11 | 3-hydroxyphenyl | H |
| 12 | 2-fluoro-5-methylphenyl | H |
| 13 | 4-chloro-3-trifluoromethylphenyl | H |
| 14 | 4-phenoxyphenyl | H |
| 15 | 4-hydroxy-3-methylphenyl | H |
| 16 | 3-(4-cyanophenoxy)phenyl | H |
| 17 | benzyl | H |

The spectral data of the above compounds are listed below.

Compound 8: 2-Chloro-N-(3-ethynylphenyl)-6,7-dimethoxyquinazoline-4-amine $^1$H NMR (400 MHz, DMSO-d$_6$): δ 3.93 (s, 3H), 3.99 (s, 3H), 4.21 (s, 1H), 7.18 (s, 1H), 7.26 (d, J=8.0 Hz, 1H), 7.43 (t, J=8.0 Hz, 1H), 7.85 (d, J=8.0 Hz, 1H), 7.89 (s, 1H), 7.94 (s, 1H), 10.00 (s, 1H); $^{13}$C NMR (100 MHz, DMSO-d$_6$): δ 56.4, 57.2, 81.1, 83.8, 103.9, 106.6, 107.9, 122.2, 123.8, 126.0, 127.6, 129.2, 139.5, 148.1, 149.5, 154.1, 155.5, 158.4; HRMS calculated for C$_{18}$H$_{14}$ClN$_3$O$_2$ (M+H): 340.0853. Found: 340.0850. Yield: 94%.

Compound 9: 2-Chloro-N-(3-ethynylphenyl)-6,7-dimethoxy-N-methyl quinazoline-4-amine $^1$H NMR (400 MHz, CDCl$_3$): δ 3.07 (s, 1H), 3.28 (s, 3H), 3.57 (s, 3H), 3.88 (s, 3H), 6.21 (s, 1H), 7.05 (s, 1H), 7.15 (d, J=7.2 Hz, 1H), 7.31-7.37 (m, 3H); $^{13}$C NMR (100 MHz, CDCl$_3$): δ 42.2, 55.2, 56.1, 78.8, 82.0, 104.8, 106.7, 108.6, 124.2, 126.7, 129.5, 130.0, 130.2, 147.5, 147.8, 150.4, 154.4, 155.0, 161.3; HRMS calculated for C$_{19}$H$_{16}$ClN$_3$O$_2$ (M+H): 354.1009. Found: 354.1016. Yield: 60%.

Compound 10: 2-Chloro-N-(3-chlorophenyl)-6,7-dimethoxyquinazoline-4-amine $^1$H NMR (400 MHz, DMSO-d$_6$): δ 3.90 (s, 3H), 3.95 (s, 3H), 7.18 (s, 1H), 7.20 (d, 1H, J=8.0 Hz), 7.44 (t, J=8.0 Hz, 1H), 7.79 (d, J=8.0 Hz, 1H), 7.95 (s, 1H), 7.97 (s, 1H), 10.08 (s, 1H); $^{13}$C NMR (100 MHz, DMSO-d$_6$): δ 56.5, 57.1, 103.3, 106.6, 107.8, 121.3, 122.4, 124.1, 130.5, 133.1, 140.7, 148.2, 149.6, 154.1, 155.6, 158.2; HRMS calculated for C$_{16}$H$_{13}$Cl$_2$N$_3$O$_2$ (M+H): 350.0463. Found: 350.0466. Yield: 75%.

Compound 11: 3-(2-Chloro-6,7-dimethoxyquinazoline-4-ylamino)phenol $^1$H NMR (400 MHz, DMSO-d$_6$): δ 3.15 (s, 1H), 3.91 (s, 3H), 3.94 (s, 3H), 6.59 (d, J=6.8 Hz, 1H), 7.13-7.21 (m, 4H), 7.98 (s, 1H), 9.96 (s, 1H); $^{13}$C NMR (100 MHz, DMSO-d$_6$): δ 56.4, 56.9, 58.5, 103.3, 106.4, 107.7, 110.6, 112.1, 114.2, 129.5, 139.8, 147.6, 149.5, 154.2, 155.4, 158.0; HRMS calculated for C$_{16}$H$_{14}$ClN$_3$O$_3$ (M+H): 332.0802. Found: 332.0810. Yield: 60%.

Compound 12: 2-Chloro-N-(2-fluoro-5-methylphenyl)-6,7-dimethoxy quinazoline-4-amine $^1$H NMR (400 MHz, DMSO-d$_6$): δ 2.32 (s, 3H), 3.87 (s, 3H), 3.92 (s, 3H), 7.12-7.16 (m, 2H), 7.22 (d, J=10.4 Hz, 1H), 7.29 (d, J=7.6 Hz, 1H), 7.90 (s, 1H), 10.05 (s, 1H); $^{13}$C NMR (100 MHz, DMSO-d$_6$): δ 20.1, 56.0, 56.3, 102.8, 105.7, 106.8, 115.61, 115.8, 124.9, 125.0, 128.1, 128.2, 128.5, 133.6, 133.7, 146.9, 149.1, 153.9, 153.9, 155.1, 156.3, 159.1; HRMS calculated for C$_{17}$H$_{15}$ClFN$_3$O$_2$ (M+H): 348.0915. Found: 348.0911. Yield: 60%.

Compound 11: 3-(2-Chloro-6,7-dimethoxyquinazoline-4-ylamino)phenol $^1$H NMR (400 MHz, DMSO-d$_6$): δ 3.92 (s, 3H), 3.96 (s, 3H), 7.19 (s, 1H), 7.75 (d, J=8.8 Hz, 1H), 7.99 (s, 1H), 8.19 (d, J=8.8 Hz, 1H), 8.42 (s, 1H), 10.32 (s, 1H); $^{13}$C NMR (100 MHz, DMSO-d$_6$): δ 56.0, 56.8, 102.8, 105.9, 107.3, 118.7, 120.9, 120.9, 121.0, 121.0, 121.5, 124.2, 124.5, 125.9, 126.2, 126.5, 126.9, 131.6, 138.3, 147.5, 149.2, 153.1, 155.2, 157.2; HRMS calculated for C$_{17}$H$_{12}$Cl$_2$F$_3$N$_3$O$_2$ (M+H): 418.0337. Found: 418.0340. Yield: 86%.

Compound 14: 2-Chloro-6,7-dimethoxy-N-(4-phenoxyphenyl)quinazoline-4-amine $^1$H NMR (400 MHz, DMSO-d$_6$): δ 3.91 (s, 3H), 3.94 (s, 3H), 7.03 (d, J=8.6 Hz, 2H), 7.07 (d, J=8.8 Hz, 2H), 7.11-7.16 (m, 2H), 7.40 (t, J=6.0 Hz, 2H), 7.71 (d, J=8.8 Hz, 2H), 7.90 (s, 1H), 9.93 (s, 1H); $^{13}$C NMR (100 MHz, DMSO-d$_6$): δ 56.5, 57.0, 103.4, 105.9, 107.5, 118.8, 119.5, 123.8, 125.3, 130.5, 134.3, 146.9, 149.5, 153.6, 153.9, 155.5, 157.4, 158.4; HRMS calculated for C$_{22}$H$_{18}$ClN$_3$O$_3$ (M+H): 408.1115. Found: 408.1121. Yield: 55%.

Compound 15: 4-(2-Chloro-6,7-dimethoxyquinazoline-4-ylamino)-3-methylphenol $^1$H NMR (400 MHz, DMSO-d$_6$): δ 2.70 (s, 3H), 3.89 (s, 3H), 3.90 (s, 3H), 6.64 (d, J=8.4 Hz, 1H), 6.71 (s, 1H), 7.04 (d, J=8.4 Hz, 1H), 7.11 (s, 1H), 7.83 (s, 1H), 9.67 (s, 1H); $^{13}$C NMR (100 MHz, DMSO-d$_6$): δ 18.5, 56.4, 56.5, 102.8, 107.0, 107.3, 113.5, 117.3, 128.0, 129.2, 136.7, 148.1, 149.2, 155.1, 155.5, 156.5, 160.1; HRMS calculated for C$_{17}$H$_{16}$ClN$_3$O$_3$ (M+H): 346.0958. Found: 346.0951. Yield: 23%.

Compound 16: 4-(3-(2-Chloro-6,7-dimethoxyquinazoline-4-ylamino)phenoxy)benzonitrile $^1$H NMR (400 MHz, DMSO-d$_6$): δ 3.91 (s, 3H), 3.94 (s, 3H), 6.94 (d, J=8.0 Hz, 1H), 7.17 (s, 1H), 7.21 (d, J=8.8 Hz, 2H), 7.50 (t, J=8.0 Hz, 1H), 7.65 (m, 2H), 7.86 (d, J=8.8 Hz, 2H), 7.90 (s, 1H), 10.00 (s, 1H); $^{13}$C NMR (100 MHz, DMSO-d$_6$): δ 56.0, 56.2, 102.1, 105.3, 106.6, 107.2, 113.8, 115.4, 118.4, 118.6, 118.7, 130.2, 134.6, 140.4, 148.2, 149.0, 153.9, 154.6, 155.0, 157.6, 160.7; HRMS calculated for C$_{23}$H$_{17}$ClN$_4$O$_3$ (M−H): 431.0911. Found: 431.0909. Yield: 74%.

Compound 17: N-Benzyl-2-chloro-6,7-dimethoxyquinazoline-4-amine $^1$H NMR (400 MHz, MeOH-d$_4$): δ 3.90 (s, 3H), 3.92 (s, 3H), 4.79 (s, 2H), 6.96 (s, 1H), 7.23 (t, J=7.2 Hz, 1H), 7.31 (t, J=7.2 Hz, 2H), 7.39 (d, J=7.2 Hz, 2H), 7.47 (s, 1H); $^{13}$C NMR (100 MHz, DMSO-d$_6$): δ 43.4, 55.8, 56.0, 102.2, 106.5, 106.8, 126.9, 127.4, 128.3, 138.9, 147.2, 148.5, 154.4, 155.0, 159.9; HRMS calculated for C$_{17}$H$_{16}$ClN$_3$O$_2$ (M+H): 330.1009. Found: 330.1007. Yield: 21%.

Embodiment 4

Synthesis of Di-Substituted Quinazoline Derivatives

The general synthesis procedure of the di-substituted quinazoline derivatives are stated as follow. Substituted phenyl amine (0.5 mmol) were added to a solution of compound 8 (0.2 mmol) in isopropyl alcohol (3 ml), followed by the addition of a drop of concentrated HCl (100 μl). The resulting solution was heated by using microwave irradiation to 150° C. for 30 min. After cooling, the mixture was filtered, and the solid was washed with isopropyl alcohol. The crude solid was dissolved in CH$_2$Cl$_2$ and washed with saturated NaHCO$_3$ solution. The organic phase was dried over MgSO$_4$, filtered and concentrated under reduced pressure. The crude residue was purified by chromatography on a silica gel column (silica gel columns 60, 0.063-0.200 mm or 0.040-0.063 mm, Merck; basic silica gel) using MeOH/CH$_2$Cl$_2$ as eluent (0% to 5%) to give compounds 18-24 (yield: 20-80%).

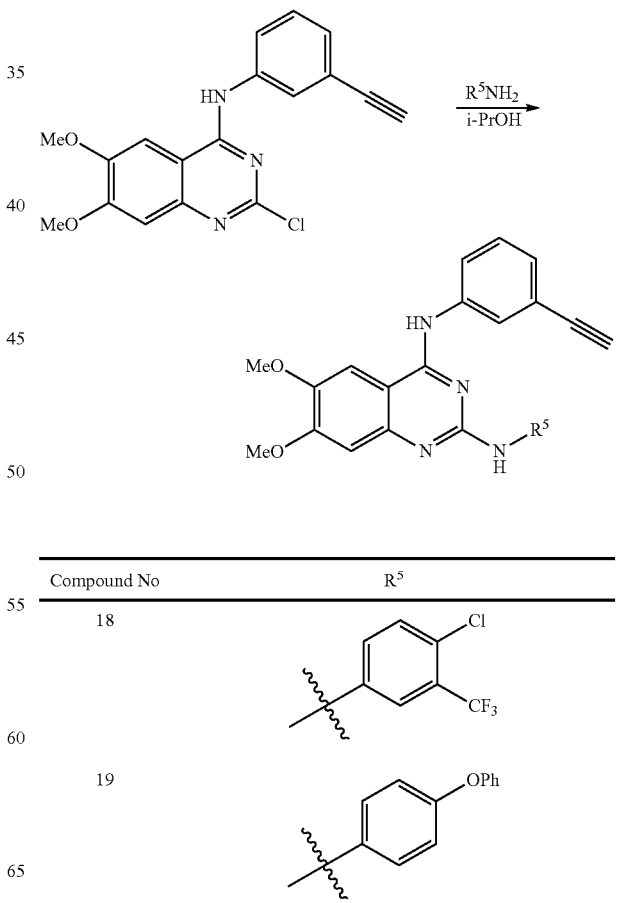

-continued
| Compound No | R⁵ |
|---|---|
| 20 | 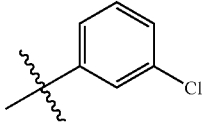 [SMILES: *c1cccc(Cl)c1] |
| 21 | 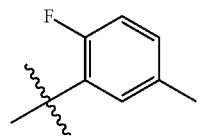 [SMILES: *c1cc(C)ccc1F] |
| 22 | 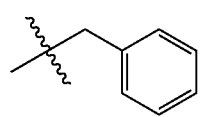 [SMILES: *Cc1ccccc1] |
| 23 | 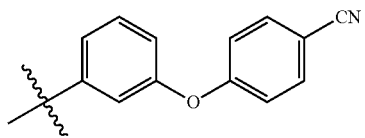 [SMILES: *c1cccc(Oc2ccc(C#N)cc2)c1] |
| 24 | 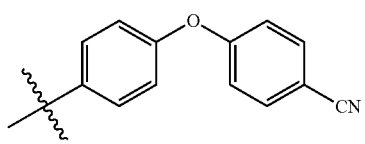 [SMILES: *c1ccc(Oc2ccc(C#N)cc2)cc1] |
| 25 | 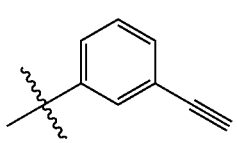 [SMILES: *c1cccc(C#C)c1] |
| 26 | 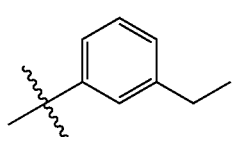 [SMILES: *c1cccc(CC)c1] |
| 27 | 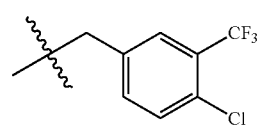 [SMILES: *Cc1ccc(Cl)c(C(F)(F)F)c1] |
| 28 | 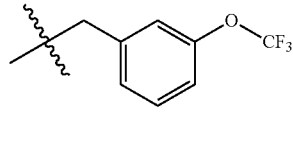 [SMILES: *Cc1cccc(OC(F)(F)F)c1] |
| 29 | 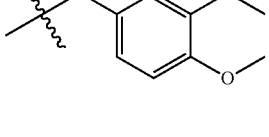 |
-continued
| Compound No | R⁵ |
|---|---|
| 30 |  |
| 31 | 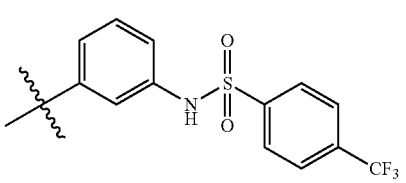 [SMILES: *c1cccc(NS(=O)(=O)c2ccc(C(F)(F)F)cc2)c1] |
| 32 | 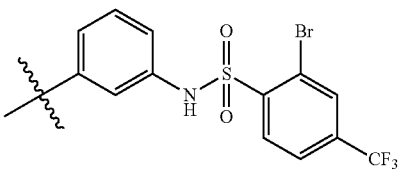 [SMILES: *c1cccc(NS(=O)(=O)c2ccc(C(F)(F)F)cc2Br)c1] |
| 33 | 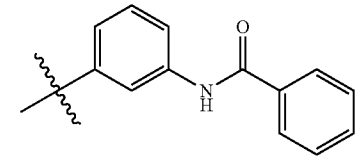 [SMILES: *c1cccc(NC(=O)c2ccccc2)c1] |
| 34 | 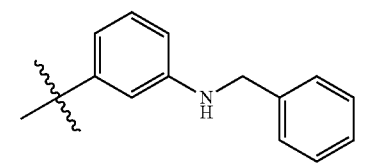 [SMILES: *c1cccc(NCc2ccccc2)c1] |
| 35 | 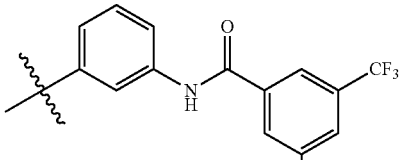 |
| 36 | 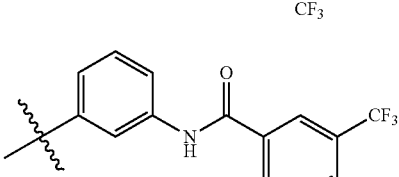 |
The spectral data of the above compounds are listed below.
Compound 18: $N^2$-(4-Chloro-3-(trifluoromethyl)phenyl)-$N^4$-(3-ethynylphenyl)-6,7-dimethoxy-quinazoline-2,4-diamine
¹H NMR (400 MHz, MeOH-d₄): δ 3.47 (s, 1H), 3.91 (s, 3H), 3.93 (s, 3H), 6.88 (s, 1H), 7.22 (d, J=7.6 Hz, 2H), 7.31 (t, J=8.0 Hz, 1H), 7.34 (d, J=9.2 Hz, 1H), 7.53 (s, 1H), 7.80 (d, J=8.0 Hz, 1H), 7.83 (s, 1H), 8.01-8.04 (m, 2H); ¹³C NMR (100 MHz, MeOH-d₄): δ 54.9, 55.4, 77.1, 77.2, 83.1, 101.9, 105.0, 105.1, 117.1-117.2 (q), 121.5, 121.7, 121.9 (d), 122.5, 122.7, 122.9, 123.3, 124.4, 125.5, 126.9, 127.3, 127.6, 128.3, 128.5, 131.17, 139.5, 140.3, 147.0, 148.3, 155.1, 155.5, 157.8; HRMS calculated for $C_{25}H_{18}ClF_3N_4O_2$ (M+H): 499.1149. Found: 499.1142. Yield: 33%.

Compound 19: $N^4$-(3-Ethynylphenyl)-6,7-dimethoxy-$N^2$-(4-phenoxyphenyl)quinazoline-2,4-diamine $^1$H NMR (400 MHz, DMSO-$d_6$): δ 3.93 (s, 3H), 3.94 (s, 3H), 4.18 (s, 1H), 6.98 (d, 4H, J=8.8 Hz), 7.13 (s, 1H), 7.15 (d, 1H, J=7.6 Hz), 7.33-7.45 (m, 6H), 7.69 (d, 1H, J=7.6 Hz), 7.75 (s, 1H), 8.10 (s, 1H), 10.33 (s, 1H), 10.90 (s, 1H); $^{13}$C NMR (100 MHz, CDCl$_3$): δ 56.1, 56.2, 77.6, 83.2, 100.0, 104.4, 106.3, 117.9, 120.0, 120.8, 122.4, 122.5, 122.7, 125.2, 127.7, 128.8, 129.5, 135.9, 138.6, 146.7, 149.2, 151.3, 155.1, 155.9, 156.9, 158.2; HRMS calculated for $C_{30}H_{24}N_4O_3$ (M+H): 489.1927. Found: 489.1925. Yield: 40%.

Compound 20: $N^2$-(3-Chlorophenyl)-$N^4$-(3-ethynylphenyl)-6,7-dimethoxy quinazoline-2,4-diamine $^1$H NMR (400 MHz, MeOH-$d_4$): δ 3.47 (s, 1H), 3.93 (s, 3H), 3.94 (s, 3H), 6.88 (d, J=8.0 Hz, 1H), 6.92 (s, 1H), 7.17 (t, J=8.0 Hz, 1H), 7.22 (d, J=7.6 Hz, 1H), 7.34 (t, J=8.0 Hz, 1H), 7.53 (d, J=8.4 Hz, 1H), 7.58 (s, 1H), 7.80 (s, 2H), 7.87 (d, J=8.4 Hz, 1H); $^{13}$C NMR (100 MHz, MeOH-$d_4$): δ 54.9, 55.4, 77.1, 83.1, 102.0, 104.9, 104.9, 117.0, 118.4, 120.5, 122.6, 123.0, 125.5, 126.9, 128.5, 129.3, 133.7, 139.6, 142.3, 146.9, 148.5, 155.1, 155.8, 157.9; HRMS calculated for $C_{24}H_{19}ClN_4O_2$ (M+H): 431.1275. Found: 431.1280. Yield: 34%.

Compound 21: $N^4$-(3-Ethynylphenylyl)-$N^2$-(2-fluoro-5-methylphenyl)-6,7-dimethoxyquinazoline-2,4-diamine $^1$H NMR (400 MHz, MeOH-$d_4$): δ 2.18 (s, 3H), 3.45 (s, 1H), 3.95 (s, 3H), 3.96 (s, 3H), 6.75 (brs, 1H), 6.91-6.98 (m, 2H), 7.23 (d, J=7.6 Hz, 1H), 7.31 (t, J=8.0 Hz, 1H), 7.62 (s, 1H), 7.75-7.77 (m, 2H), 7.91 (d, J=7.6 Hz, 1H); $^{13}$C NMR (100 MHz, CDCl$_3$): δ 21.2, 56.1, 56.1, 75.5, 100.3, 104.4, 105.5, 114.0, 114.2, 121.4, 122.2, 122.3, 122.7, 122.7, 125.3, 127.6, 127.7, 127.8, 128.9, 133.7, 133.7, 138.6, 146.9, 148.1, 149.7, 152.1, 155.2, 155.2, 157.1; HRMS calculated for $C_{25}H_{21}FN_4O_2$ (M+H): 429.1727. Found: 429.1721. Yield: 20%.

Compound 22: $N^2$-Benzyl-$N^4$-(3-ethynylphenyl)-6,7-dimethoxy quinazoline-2,4-diamine $^1$H NMR (400 MHz, DMSO-$d_6$): δ 3.84 (s, 3H), 3.85 (s, 3H), 4.15 (s, 1H), 4.53 (d, J=6.4 Hz, 2H), 6.75 (s, 1H), 7.10-7.19 (m, 3H), 7.27 (t, J=8.0 Hz, 1H), 7.28 (d, J=7.2 Hz, 2H), 7.33 (d, J=7.2 Hz, 2H), 7.63 (s, 1H), 7.90 (s, 1H), 9.14 (s, 1H); $^{13}$C NMR (100 MHz, CDCl$_3$): δ 29.3, 45.2, 55.7, 55.9, 76.8, 83.0, 100.1, 103.4, 105.2, 121.6, 122.2, 124.2, 126.7, 126.9, 127.1, 128.1, 128.4, 138.5, 139.3, 145.7, 154.7, 156.5, 158.0; HRMS calculated for $C_{25}H_{22}N_4O_2$ (M+H): 411.1821. Found: 411.1826. Yield: 15%.

Compound 23: 4-(3-(4-(3-Ethynylphenylamino)-6,7-dimethoxyquinazolin-2-ylamino)phenoxy)benzonitrile $^1$H NMR (400 MHz, CDCl$_3$): δ 3.05 (s, 1H), 3.93 (s, 3H), 3.95 (s, 3H), 6.61 (d, J=7.6 Hz, 1H), 6.92 (s, 1H), 6.94 (s, 1H), 7.01 (d, J=9.2 Hz, 2H), 7.20 (d, J=7.6 Hz, 1H), 7.26 (t, J=8.0 Hz, 2H), 7.35 (d, J=7.2 Hz, 2H), 7.54 (d, J=9.2 Hz, 2H), 7.64 (s, 1H), 7.66 (d, J=8.0 Hz, 1H), 7.73 (s, 1H); $^{13}$C NMR (100 MHz, CDCl$_3$): δ 56.1, 56.2, 77.6, 83.2, 100.1, 104.6, 105.3, 106.3, 110.5, 112.8, 115.2, 118.0, 119.0, 122.7, 122.8, 125.4, 127.9, 128.8, 130.1, 133.9, 138.5, 142.1, 147.0, 148.9, 155.1, 155.1, 155.3, 157.0, 161.6; HRMS calculated for $C_{31}H_{23}N_5O_3$ (M+H): 514.1879. Found: 514.1888. Yield: 80%.

Compound 24: 4-(4-(4-(3-Ethynylphenylamino)-6,7-dimethoxyquinazolin-2-ylamino)phenoxy)benzonitrile $^1$H NMR (400 MHz, DMSO-$d_6$): δ 3.92 (s, 3H), 3.94 (s, 3H), 4.22 (s, 1H), 7.06 (d, J=8.4 Hz, 2H), 7.10-7.15 (m, 3H), 7.36 (d, J=7.6 Hz, 1H), 7.43 (t, J=8.0 Hz, 1H), 7.53 (d, J=7.6 Hz, 2H), 7.68 (d, J=7.6 Hz, 1H), 7.74 (s, 1H), 7.85 (d, J=8.4 Hz, 2H), 8.03 (s, 1H); $^{13}$C NMR (100 MHz, CDCl$_3$): δ 56.1, 56.2, 77.6, 83.2, 100.2, 104.6, 105.0, 106.3, 117.3, 119.0, 120.6, 121.0, 122.6, 122.7, 125.5, 127.8, 128.8, 134.0, 137.6, 138.6, 146.8, 148.6, 149.2, 155.1, 155.7, 157.0, 162.4; HRMS calculated for $C_{31}H_{23}N_5O_3$ (M+H): 514.1879. Found: 514.1876. Yield: 75%.

Compound 25: $N^2$,$N^4$-Bis(3-ethynylphenyl)-6,7-dimethoxyquinazoline-2,4-diamine $^1$H NMR (400 MHz, DMSO-$d_6$) δ 3.92 (s, 3H, OCH$_3$), 3.94 (s, 3H, OCH$_3$), 4.22 (s, 1H), 4.24 (s, 1H), 7.13 (s, 1H, ArH), 7.25 (d, J=8.0 Hz, 1H, ArH), 7.32-7.36 (m, 2H, ArH), 7.44 (t, J=8.0 Hz, 1H, ArH), 7.53 (s, 2H, ArH), 7.69 (s, 1H, ArH), 7.73 (d, J=8.0 Hz, 1H, ArH), 8.05 (s, 1H, ArH); $^{13}$C NMR (100 MHz, CDCl$_3$) δ 56.0, 56.1, 77.0, 77.54, 83.3, 83.9, 100.1, 104.5, 106.2, 119.7, 122.2, 122.2, 122.5, 122.6, 125.0, 125.4, 127.6, 128.7, 128.9, 138.6, 140.1, 146.7, 148.9, 154.9, 155.4, 156.8; HRMS calculated for $C_{26}H_{20}N_4O_2$ [M$^+$+H] 421.1665. found 421.1671.

Compound 26: $N^2$-(3-ethylphenyl)-$N^4$-(3-ethynylphenyl)-6,7-dimethoxy quinazoline-2,4-diamine $^1$H NMR (400 MHz, DMSO-$d_6$) δ 1.09 (t, J=7.6 Hz, 3H, CH$_3$), 2.52 (q, J=7.6 Hz, 2H, CH$_2$), 3.92 (s, 3H, OCH$_3$), 3.93 (s, 3H, OCH$_3$), 4.23 (s, 1H), 7.00 (d, J=6.8 Hz, 1H, ArH), 7.11 (s, 1H, ArH), 7.23-7.27 (m, 3H, ArH), 7.37-7.43 (m, 2H, ArH), 7.71 (d, J=8.0 Hz, 1H, ArH), 7.74 (s, 1H, ArH), 8.06 (s, 1H, ArH); $^{13}$C NMR (100 MHz, DMSO-$d_6$) δ 15.3, 28.0, 56.2, 56.3, 81.1, 82.8, 98.5, 102.9, 105.0, 119.1, 120.8, 122.1, 124.0, 125.5, 127.8, 128.7, 128.9, 129.1, 135.8, 136.6, 137.4, 144.6, 147.2, 150.6, 155.9, 158.5; HRMS calculated for $C_{26}H_{24}N_4O_2$ [M$^+$+H] 425.1978. found 425.1978.

Compound 27: $N^2$-(4-Chloro-3-(trifluoromethyl)benzyl)-$N^4$-(3-ethynyl phenyl)-6,7-dimethoxyquinazoline-2,4-diamine $^1$H NMR (400 MHz, MeOH-$d_4$) δ 3.43 (s, 1H), 3.91 (s, 3H, OCH$_3$), 3.92 (s, 3H, OCH$_3$), 4.62 (s, 2H, CH$_2$), 6.84 (s, 1H, ArH), 7.17 (d, J=8.0 Hz, 1H, ArH), 7.22 (t, J=8.0 Hz, 1H), 7.45 (d, J=8.0 Hz, 1H, ArH), 7.50 (d, J=7.6 Hz, 1H, ArH), 7.56 (s, 1H, ArH), 7.62 (d, J=8.0 Hz, 1H, ArH), 7.70 (s, 1H, ArH), 7.86 (s, 1H, ArH); $^{13}$C NMR (100 MHz, CDCl$_3$) δ 44.5, 56.0, 56.2, 78.2, 83.2, 100.3, 103.9, 105.6, 121.4, 121.9, 122.6, 124.1, 124.9, 126.44-126.48 (t), 127.5, 127.6, 127.9, 128.6, 130.4, 131.3, 131.6, 138.6, 139.3, 146.3, 155.1, 157.0, 158.1; HRMS calculated for $C_{26}H_{20}ClF_3N_4O_2$ [M$^+$+H] 513.1305. found 513.1309.

Compound 28: $N^4$-(3-Ethynylphenyl)-6,7-dimethoxy-$N^2$-(3-(trifluoro methoxy)benzyl)quinazoline-2,4-diamine $^1$H NMR (400 MHz, MeOH-d$_4$) δ 3.42 (s, 1H), 3.88 (s, 3H, OCH$_3$), 3.90 (s, 3H, OCH$_3$), 4.61 (s, 2H, CH$_2$), 6.81 (s, 1H, ArH), 7.05 (d, J=7.6 Hz, 1H, ArH), 7.14 (d, J=7.6 Hz, 1H, ArH), 7.17-7.21 (m, 2H, ArH), 7.30 (s, 1H, ArH), 7.32 (t, J=7.6 Hz, 1H, ArH), 7.51 (s, 1H, ArH), 7.66 (d, J=7.6 Hz, 1H, ArH), 7.87 (s, 1H, ArH); $^{13}$C NMR (100 MHz, MeOH-d$_4$) δ 45.3, 56.2, 56.8, 78.1, 84.3, 103.6, 105.1, 105.3, 119.8, 120.4, 120.4, 122.9, 123.6, 123.7, 126.5, 126.6, 127.9, 129.3, 130.6, 140.7, 144.6, 147.2, 149.9, 150.4, 150.4, 156.2, 159.1, 159.8; HRMS calculated for $C_{26}H_{21}F_3N_4O_3$ [M$^+$+H] 549.1644. found 549.1639.

Compound 29: $N^2$-(3,4-dimethoxybenzyl)-$N^4$-(3-ethynylphenyl)-6,7-dimethoxyquinazoline-2,4-diamine $^1$H NMR (400 MHz, MeOH-d$_4$) δ 3.45 (s, 1H), 3.69 (s, 3H, OCH$_3$), 3.75 (s, 3H, OCH$_3$), 3.90 (s, 3H, OCH$_3$), 3.93 (s, 3H, OCH$_3$), 4.52 (s, 2H, CH$_2$), 6.83-6.88 (m, 3H, ArH), 6.95 (s, 1H, ArH), 7.17 (dt, J=8.0 Hz, 1H, ArH), 7.25 (t, J=8.0 Hz, 1H, ArH), 7.56 (s, 1H, ArH), 7.74 (d, 1H, ArH), 7.96 (s, 1H, ArH); $^{13}$C NMR (100 MHz, CDCl$_3$) δ 14.1, 29.6, 44.7, 55.8, 56.2, 61.6, 77.3, 83.0, 102.4, 102.8, 110.7, 111.0, 119.4, 122.6, 122.9, 125.1, 128.3, 128.7, 130.8, 138.2, 146.7, 148.2, 149.0, 155.7, 157.6, 165.2, 165.7; HRMS calculated for $C_{27}H_{26}N_4O_4$ [M$^+$+H] 471.2032. found 471.2031.

Compound 30: N-(3-(4-(3-ethynylphenylamino)-6,7-dimethoxyquinazolin-2-ylamino)phenyl)benzenesulfonamide $^1$H NMR (400 MHz, MeOH-d$_4$) δ 3.47 (s, 1H), 3.77 (s, 3H), 3.86 (s, 3H), 6.66 (d, J=8.0 Hz, 1H), 6.82 (s, 1H), 7.04 (t, J=8.0 Hz, 1H), 7.19 (d, J=8.0 Hz, 1H), 7.26 (t, J=8.0 Hz, 1H), 7.30 (d, J=8.0 Hz, 1H), 7.40 (t, J=8.0 Hz, 3H), 7.46-7.48 (m, 2H), 7.53 (s, 1H), 7.75 (m, 4H); $^{13}$C NMR (100 MHz, MeOH-d$_4$) δ 56.3, 56.8, 78.8, 84.4, 103.4, 104.7, 105.7, 113.4, 115.6, 117.5, 123.9, 124.6, 127.0, 128.2, 128.7, 129.8, 129.9, 130.3, 133.8, 139.3, 140.4, 141.0, 141.8, 146.5, 148.3, 155.7, 156.6, 159.13; HRMS calcd for $C_{30}H_{25}N_5O_4S$ [M$^+$+H] 552.1627. found 552.1707. Yield: 45%.

Compound 31: N-(3-(4-(3-Ethynylphenylamino)-6,7-dimethoxyquinazolin-2-ylamino)phenyl)-3-(trifluoromethyl)benzenesulfonamide $^1$H NMR (400 MHz, DMSO-d$_6$) δ 3.94 (s, 6H), 4.23 (s, 1H), 6.88 (d, $^1$H NMR (400 MHz, MeOH-d$_4$) δ, 1H), 7.13 (s, 2H), 7.19 (t, J=8.0 Hz, 1H), 7.35-7.43 (m, 3H), 7.70-7.73 (m, 2H), 7.78 (t, J=8.0 Hz, 1H), 8.01 (d, J=8.0 Hz, 1H), 8.05-8.07 (m, 2H), 8.11 (s, 1H); $^{13}$C NMR (100 MHz, DMSO-d$_6$) δ 56.7, 57.1, 81.6, 83.3, 99.3, 103.6, 105.4, 114.2, 115.0, 116.8, 118.9, 122.3, 122.4, 122.8, 123.6, 124.0, 125.1, 125.8, 126.3, 127.8, 128.0, 129.3, 129.8, 129.9, 130.1, 130.4, 130.8, 131.2, 131.4, 136.8, 137.9, 138.2, 141.0, 147.8, 151.1, 156.3, 158.8, 158.9; HRMS calcd for $C_{31}H_{24}F_3N_6O_4S$ [M$^+$+H] 620.1501. found 620.1546. Yield: 30%.

Compound 32: 2-Bromo-N-(3-(4-(3-ethynylphenylamino)-6,7-dimethoxy quinazolin-2-ylamino)phenyl)-4-(trifluoromethyl)benzenesulfonamide $^1$H NMR (400 MHz, MeOH-d$_4$) δ 3.46 (s, 1H), 3.94 (s, 6H), 6.73 (d, J=8.0 Hz, 1H), 7.00 (s, 1H), 7.06 (t, J=8.0 Hz, 1H), 7.20 (d, J=8.0 Hz, 1H), 7.29-7.35 (m, 2H), 7.59 (s, 1H), 7.69 (d, J=8.4 Hz, 1H), 7.74 (s, 1H), 7.80 (s, 1H), 7.87 (d J=8.4 Hz, 1H), 8.01 (s, 1H), 8.26 (d, J=8.4 Hz, 1H); $^{13}$C NMR (100 MHz, MeOH-d$_4$) δ 56.4, 56.8, 78.6, 84.4, 103.4, 106.3, 106.4, 112.6, 114.6, 117.0, 121.8, 122.5, 123.9, 124.3, 125.2, 125.6, 125.7, 126.7, 128.2, 129.8, 130.2, 133.2, 133.3, 134.3, 135.9, 136.2, 138.0, 141.0, 143.1, 143.7, 148.2, 149.6, 156.4, 157.1, 159.2; HRMS calcd for $C_{31}H_{23}BrF_3N_6O_4S$ [M$^+$+H] 698.0606. found 698.0682. Yield: 40%.

Compound 33: N-(3-(4-(3-ethynylphenylamino)-6,7-dimethoxy quinazolin-2-ylamino)phenyl)benzamide $^1$H NMR (400 MHz, DMSO-d$_6$) δ 3.49 (s, 6H), 4.24 (s, 1H), 7.14 (s, 1H), 7.29-7.39 (m, 3H), 7.51-7.62 (m, 5H), 7.79 (s, 2H), 7.88 (s, 1H), 7.94 (d, J=8.0 Hz, 2H), 8.13 (s, 1H); $^{13}$C NMR (100 MHz, MeOH-d$_4$) δ 55.7, 56.1, 80.6, 82.4, 98.3, 102.5, 104.4, 113.7, 116.5, 117.4, 121.4, 124.8, 127.0, 127.1 (2C), 127.8 (2C), 128.3, 128.5, 131.1, 134.2, 135.5, 136.2, 136.9, 139.2, 139.2, 146.7, 150.3, 155.4, 157.8, 165.0; HRMS calcd for $C_{31}H_{26}N_6O_3$ [M$^+$+H] 516.1957. found 516.2025. Yield: 70%.

Compound 34: $N^2$-(3-(benzylamino)phenyl)-$N^4$-(3-ethynylphenyl)-6,7-dimethoxyquinazoline-2,4-diamine $^1$H NMR (400 MHz, CDCl3) δ 3.02 (s, 1H), 3.78 (s, 3H), 3.96 (s, 3H), 4.23 (s, 2H), 6.24 (d, J=8.0 Hz, 1H), 6.72-6.78 (m, 2H), 6.92-7.12 (m, 5H), 7.18-7.45 (m, 8H), 7.72 (d, J=8.0 Hz, 1H), 7.85 (s, 1H); 13C NMR (100 MHz, CDCl3) δ 29.4, 55.9, 56.0, 76.1, 83.0, 102.0, 104.0, 104.6, 106.6, 109.2, 121.0, 122.3, 123.9, 126.4, 126.9, 127.4, 127.9, 128.3, 128.5, 129.3, 137.3, 138.5, 139.2, 139.3, 139.7, 146.7, 148.7, 155.3, 157.8; HRMS calcd for $C_{31}H_{27}N_5O_2$ [M$^+$+H] 502.2243. found 502.2245. Yield: 45%.

Compound 35: N-(3-(4-(3-ethynylphenylamino)-6,7-dimethoxyquinazolin-2-ylamino)phenyl)-3,5-bis(trifluoromethyl)benzamide $^1$H NMR (400 MHz, CDCl$_3$) δ 2.94 (s, 1H), 3.66 (s, 3H), 3.77 (s, 3H), 6.66 (s, 1H), 6.93 (d, J=8.0 Hz, 1H), 6.97 (d, J=8.0 Hz, 1H), 7.08 (t, J=8.0 Hz, 2H), 7.12-7.20 (m, 2H), 7.54 (d, J=8.0 Hz, 1H), 7.78 (s, 1H), 7.95 (brs, 1H), 8.01-8.05 (m, 2H), 8.28 (s, 2H), 8.39 (s, 1H); $^{13}$C NMR (100 MHz, CDCl$_3$) δ 55.9, 56.1, 77.6, 83.1, 100.8, 104, 3, 104.8 (q), 112.2, 115.0, 116.4, 121.5, 122.3, 122.6, 124.2, 125.2 (q), 125.3, 126.9, 127.5 (q), 128.6, 129.3, 131.7, 131.7, 132.1, 132.4, 132.7, 137.0, 137.1, 138.6, 140.3, 146.9, 154.3, 155.2, 156.8, 163.2; HRMS calcd for $C_{33}H_{23}F_6N_5O_3$ [M$^+$+H] 652.1783. found 652.1777. Yield: 30%.

Compound 36: N-(3-(4-(3-ethynylphenylamino)-6,7-dimethoxyquinazolin-2-ylamino)phenyl)-3-(trifluoromethyl)benzamide $^1$H NMR (400 MHz, MeOH-d$_4$) δ 3.41 (s, 1H), 3.78 (s, 3H), 3.84 (s, 3H), 6.80 (s, 1H), 7.01 (d, J=8.0 Hz, 1H), 7.14-27 (m, 3H), 7.35 (d, J=8.0 Hz, 1H), 7.45 (s, 1H), 7.66 (t, J=8.0 Hz, 1H), 7.81-7.88 (m, 3H), 8.05 (s, 1H), 8.11 (d, J=8.0 Hz, 1H), 8.21 (s, 1H); $^{13}$C NMR (100 MHz, MeOH-d$_4$) δ 56.2, 56.7, 78.5, 84.5, 103.2, 106.1, 113.4, 113.8, 113.9, 115.8, 117.3, 123.7, 124.0, 124.1, 125.6 (q), 126.5, 126.6, 126.7, 128.0, 129.1, 129.4, 129.5, 129.8, 130.5, 131.4, 131.73, 132.0, 132.2, 132.3, 137.3, 137.4, 139.6, 140.9, 142.4, 147.9, 149.5, 156.2, 157.1, 158.7, 166.9; HRMS calcd for $C_{32}H_{24}F_3N_5O_3$ 584.1909. found 584.1918.

Embodiment 5

Synthesis of Di-Substituted Quinazoline Derivatives

The general synthesis procedure of the di-substituted quinazoline derivatives are stated as follow.

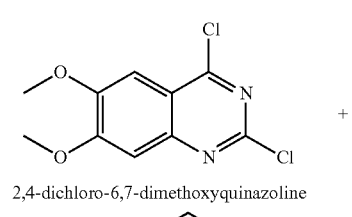

2,4-dichloro-6,7-dimethoxyquinazoline

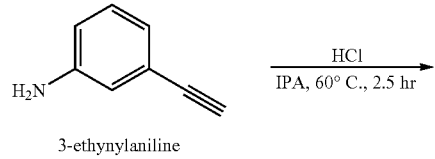

3-ethynylaniline

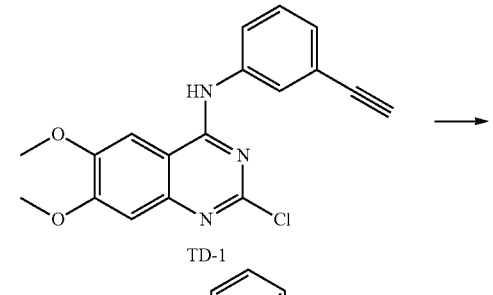

TD-1

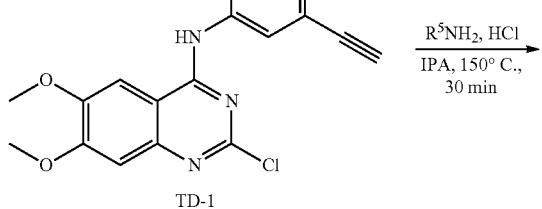

TD-1

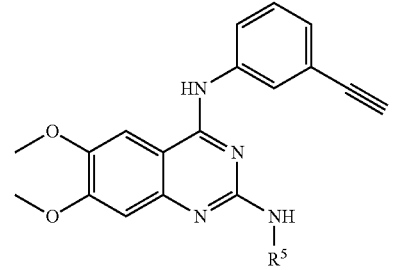

87-90, 95, 96

A solution of 2,4-dichloro-6,7-dimethoxyquinazoline in isopropyl alcohol (IPA) was treated with 3-ethynylaniline and a drop of concentrated HCl and then stirred at 60° C. for 2.5 h to provide TD-1. A series of phenoxyanilines was added to a solution of TD-1 in IPA, followed by the addition of concentrated HCl. The mixture was heated under microwave radiation at 150° C. for 30 min to obtain compounds 87~90, 95 and 96.

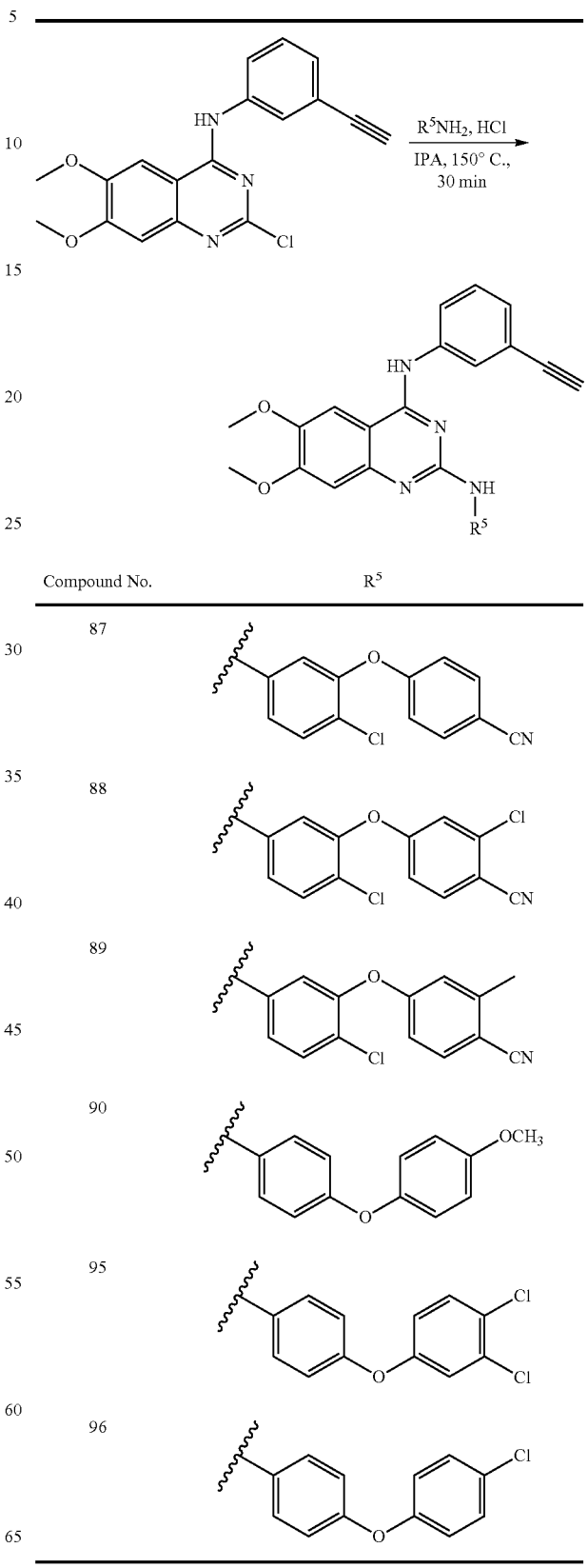

The spectral data of the above compounds are listed below.

Compound 87: 4-(2-chloro-5-((4-((3-ethynylphenyl)amino)-6,7-dimethoxyquinazolin-2-yl)amino)phenoxy)benzonitrile $^1$H NMR (400 MHz, DMSO-d$_6$) d 3.92 (s, 3H), 3.94 (s, 3H), 4.22 (s, 1H), 7.00 (d, J=9.2 Hz, 2H), 7.09 (s, 1H), 7.27 (d, J=7.6 Hz, 1H), 7.34 (t, J=8.4 Hz, 1H), 7.45-7.50 (m, 2H), 7.55 (d, J=8.8 Hz, 1H), 7.68 (s, 2H), 7.82 (dt, J=9.2, 2.4 Hz, 2H), 8.05 (s, 1H), 10.50 (s, 1H), 10.85 (s, 1H).

Compound 88: 2-chloro-4-(2-chloro-5-((4-((3-ethynylphenyl)amino)-6,7-dimethoxyquinazolin-2-yl)amino)phenoxy)benzonitrile $^1$H NMR (400 MHz, DMSO-d$_6$) d 3.92 (s, 3H), 3.93 (s, 3H), 4.20 (s, 1H), 6.93 (dd, J=8.8, 2.4 Hz, 1H), 7.08 (s, 1H), 7.23 (s, 1H), 7.25 (d, J=2.4 Hz, 1H), 7.34 (t, J=8.0 Hz, 1H), 7.43 (dd, J=8.8, 2.0 Hz, 1H), 7.56 (d, J=8.8 Hz, 2H), 7.66 (d, J=1.2 Hz, 2H), 7.92 (d, J=8.8 Hz, 1H), 8.11 (s, 1H), 10.70 (s, 1H), 11.05 (s, 1H).

Compound 89: 4-(2-chloro-5-((4-((3-ethynylphenyl)amino)-6,7-dimethoxyquinazolin-2-yl)amino)phenoxy)-2-methylbenzonitrile $^1$H NMR (400 MHz, DMSO-d$_6$) d 2.43 (s, 3H), 3.92 (s, 3H), 3.93 (s, 3H), 4.22 (s, 1H), 6.77 (dd, J=8.4, 2.4 Hz, 1H), 6.94 (d, J=2.4 Hz, 1H), 7.08 (s, 1H), 7.26 (d, J=7.6 Hz, 1H), 7.33 (t, J=7.6 Hz, 1H), 7.41-7.45 (m, 2H), 7.53 (d, J=8.4 Hz, 1H), 7.66 (s, 1H), 7.67 (s, 1H), 7.72 (d, J=8.8 Hz, 1H), 8.12 (s, 1H), 10.67 (s, 1H), 11.04 (s, 1H).

Compound 90: N$^2$-(4-(3,4-dichlorophenoxyl)phenyl)-N$^4$-(3-ethynylphenyl)-6,7-dimethoxyquinazoline-2,4-diamine $^1$H NMR (400 MHz, DMSO-d$_6$) d 3.36 (s, 3H), 3.92 (s, 3H), 3.93 (s, 3H), 4.20 (s, 1H), 6.90 (d, J=8.8 Hz, 2H), 6.97 (s, 4H), 7.09 (s, 1H), 7.34-7.40 (m, 4H), 7.69 (d, J=7.2 Hz, 1H), 7.77 (s, 1H), 8.15 (s, 1H), 10.36 (s, 1H), 11.00 (s, 1H).

Compound 95: N$^2$-(4-(3,4-dichlorophenoxyl)phenyl)-N$^4$-(3-ethynylphenyl)-6,7-dimethoxyquinazoline-2,4-diamine $^1$H NMR (400 MHz, DMSO-d$_6$) d 3.94 (s, 6H), 4.20 (s, 1H), 6.97 (dd, J=8.8, 2.8 Hz, 1H), 7.07 (d, J=8.8 Hz, 2H), 7.13 (s, 1H), 7.23 (d, J=2.8 Hz, 1H), 7.35 (dt, J=7.6, 1.2 Hz, 1H), 7.42 (t, J=7.6 Hz, 1H), 7.49 (d, J=8.8 Hz, 2H), 7.63 (d, J=8.8 Hz, 1H), 7.69 (d, J=7.6 Hz, 1H), 7.76 (s, 1H), 8.10 (s, 1H), 10.38 (s, 1H), 10.92 (s, 1H).

Compound 96: N$^2$-(4-(4-chlorophenoxyl)phenyl)-N$^4$-(3-ethynylphenyl)-6,7-dimethoxyquinazoline-2,4-diamine $^1$H NMR (400 MHz, DMSO-d$_6$) d 3.93 (s, 3H), 3.94 (s, 3H), 4.20 (s, 1H), 6.98-7.03 (m, 4H), 7.14 (s, 1H), 7.37 (t, J=7.6 Hz, 1H), 7.40-7.48 (m, 5H), 7.69 (d, J=8.0 Hz, 1H), 7.76 (s, 1H), 8.08 (s, 1H), 10.33 (s, 1H), 10.88 (s, 1H).

Embodiment 6

Synthesis of Di-Substituted Quinazoline Derivatives

The R$^4$ and R$^5$ listed in the Table below can be paired arbitrarily.

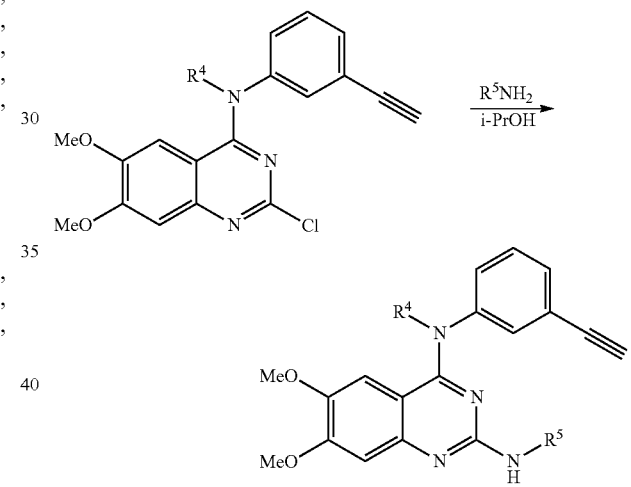

| R$^4$ | R$^5$ |
|---|---|
| 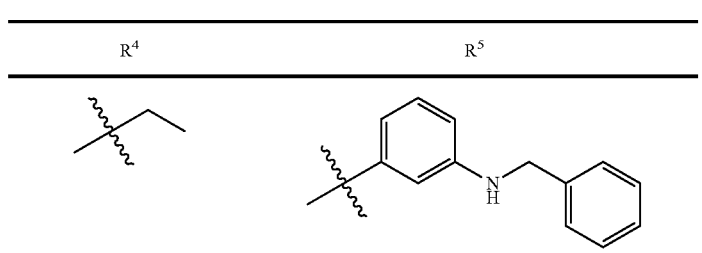 | |
| 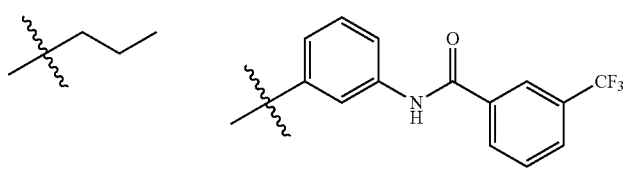 | |

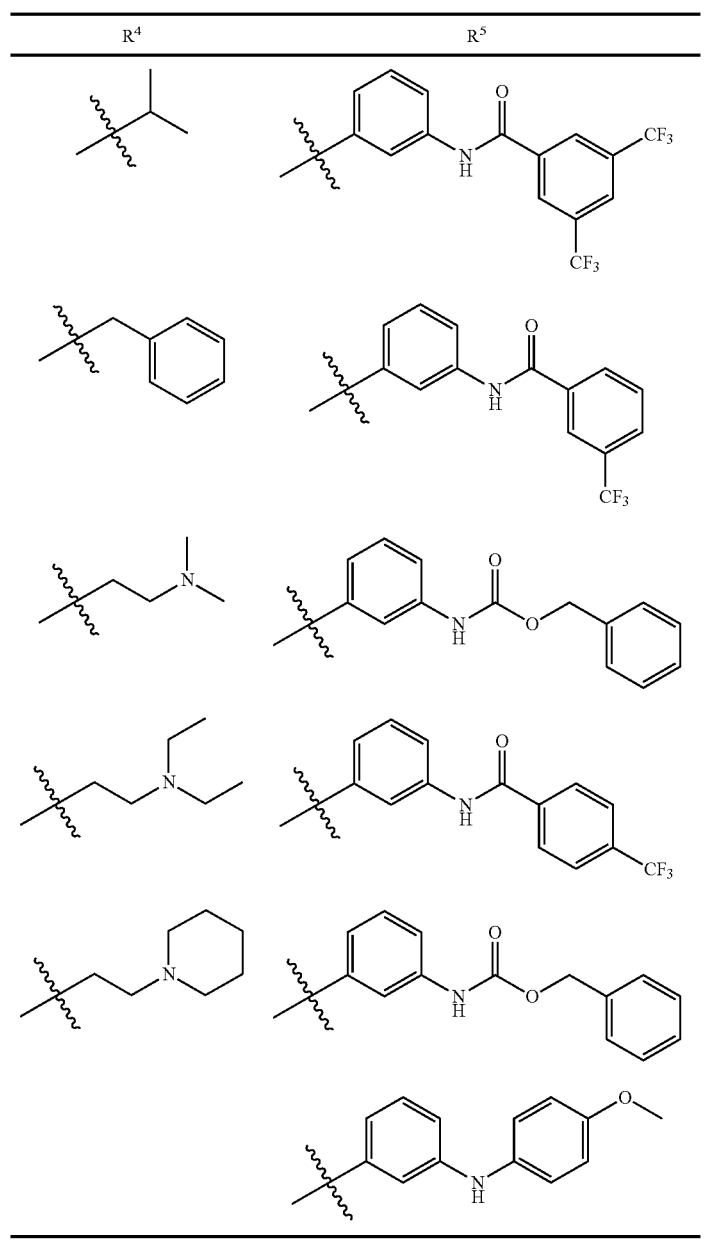
Pharmaceutical Composition and Medical Application Thereof
In one aspect, the present invention directs to a pharmaceutical composition. The pharmaceutical composition comprises an effective amount of a compound having a chemical structure (I), (II), (III), or (VII) below and a pharmaceutically acceptable carrier.
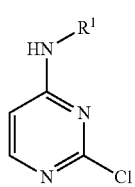
(I)
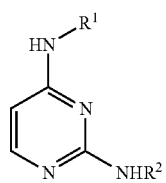
(II)
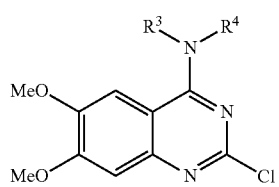
(III)

-continued (VII)

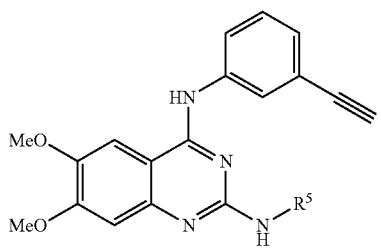

The R³ above is

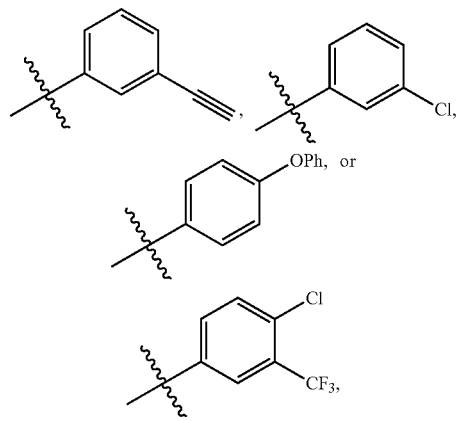

and R⁴ is H or methyl group. The R⁵ above is

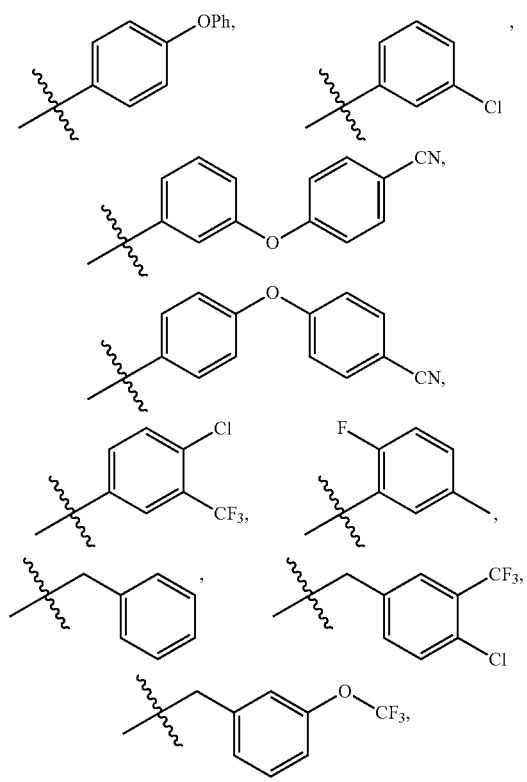

-continued

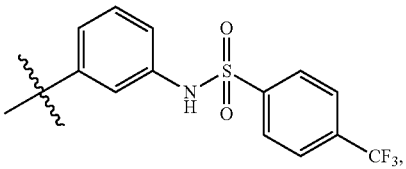

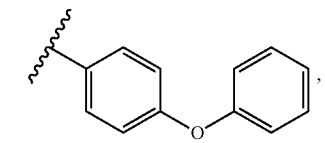

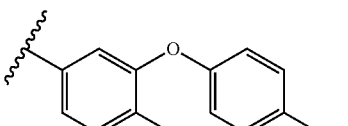

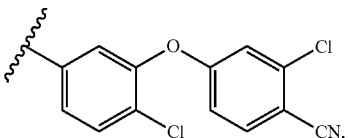

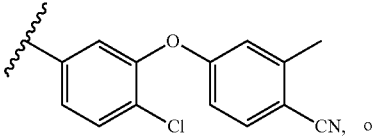

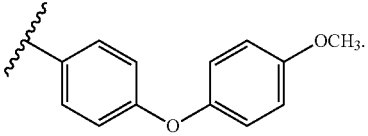

In another aspect, the present invention directs to a method of inhibiting the expression of cancerous inhibitor of PP2A. The method comprises contacting a cell with an effective amount of a compound having the chemical structure (I), (II), (III), or (VII) above.

In yet another aspect, the present invention directs to a method of treating cancer. The method comprises administrating an effective amount of a compound having a chemical structure (I), (II), (III), or (VII) above by a needed subject. The cancer above can be a hepatocellular carcinoma or a lung cancer.

Inhibition of EGFR Kinase Activation

Quinazolines have been used as a scaffold for synthesizing a variety of pharmacological compounds. For example, antagonists of human adenosine A3 receptor, inhibitors of histone lysine methyltransferase G9a, inhibitors of poly (ADP-ribose)polymerase, an inhibitor of protein kinase c isotypes, agonists of histamine H4 receptor and inhibitors of thymidylate synthase inhibitors. Some quinazoline derivatives having amino substitutes at position 4 of the quinazoline structure have been demonstrated to be inhibitors of epidermal growth factor receptor (EGFR) kinase. EGFR kinase is a receptor tyrosine kinase, which regulates cell proliferation. The numbering of quinazoline is shown below.

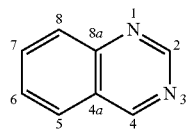

Some quinazoline derivatives having amino substitutes at position 4, such as erlotinb, gefitinib, and lapatinib, have been approved for clinical use in cancer patients. The chemical structure of compound 8 is similar to erlotinb (FIG. 1). A chloride atom at the 2-position of the quinazoline ring was further introduced to prevent the formation of hydrogen bonds between nitrogen atoms of compound 8 and T790 and M793 of EGFR kinase. A comparison of inhibiting the EGFR kinase activity by erlotinib and compound 8 in PC9 cells (a human lung adenocarcinoma) and H358 cells (a lung cancer cell line) was made by western blot.

Figure 1B:
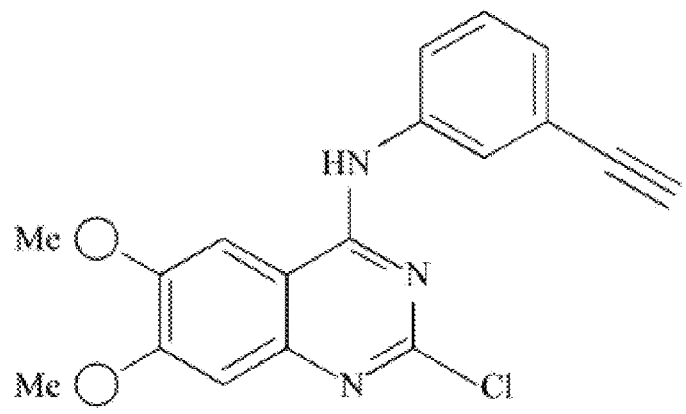
Figure 1B:
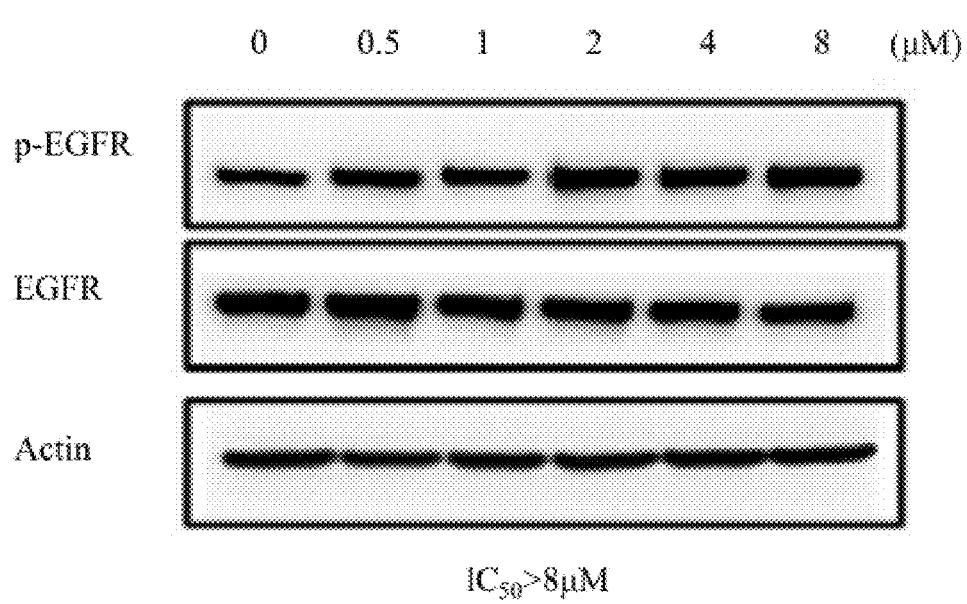

PC9 cells ($3 \times 10^5$ cells) were treated with erlotinb or compound 8 at 0.5, 1, 2, 4, and 8 µM in 60 mm dishes for 24 hours. 40 µg/per lane of cell lysates were analyzed by western blot. The antibodies of actin, EGFR, and p-EGFR were from Cell Signaling (Danvers, Mass.). The results of western blot are shown in FIGS. 1A-1B. In FIGS. 1A-1B, actin lines are used to show an internal standard for the loading control in this western blot. The result of FIG. 1A shows that erlotinib was able to inhibit the phosphorylation of EGFR with $IC_{50}$ at 1.36 µM, but the result of FIG. 1B shows that compound 8 was devoid of EGFR kinase inhibition.

Figure 1C:
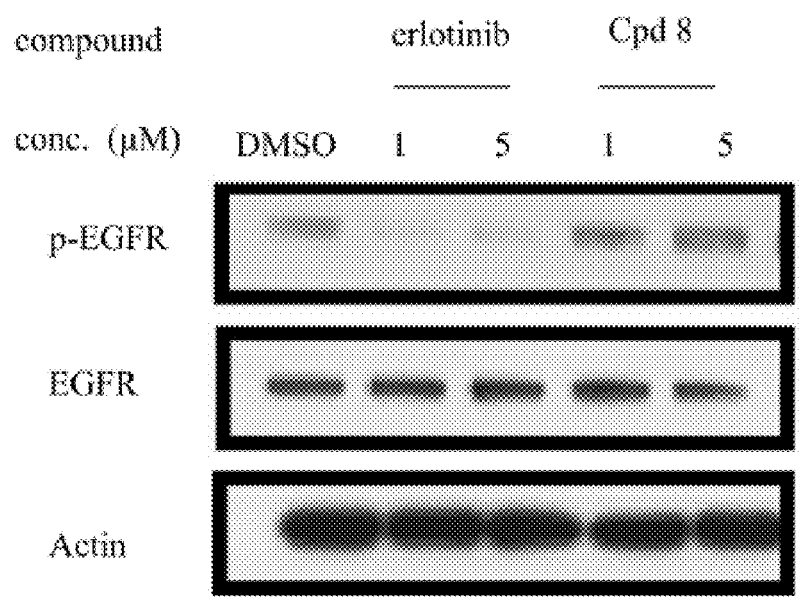
FIG. 1C is the western blot analysis of inhibiting EGFR phosphorylation activity by erlotinib and compound 8 in H358 cells (a lung cancer cell line), respectively. D denotes DMSO.

H358 cells were exposed to erlotinib or compound 8 at 1, and 5 µM for 24 hours and cell lysates were analyzed for EGFR phosphorylation. The result is shown in FIG. 1C. The result of FIG. 1C also shows that erlotinib was able to inhibit the phosphorylation of EGFR, but compound 8 was devoid of EGFR kinase inhibition.

The results above suggested that functional group connected to 2-position of quinazoline ring impeded nitrogen atom of quinazoline to act as a hydrogen acceptor and break the binding with EGFR. Therefore, a series of quinazoline derivatives (compounds 8-17) having a substituent at the 2 position of the quinazoline skeleton were synthesized. Another series of quinazoline derivatives (compounds 18-33) having various phenyl amine substituents at the position 2 of quinazoline were further synthesized. Moreover, the quinazoline skeleton was further simplified by using pyrimidine skeleton instead (compounds 1-7). The bioactivity of these compounds were analyzed and described below.

Structure Activity Relationship of Pyrimidine and Quinazoline Derivatives

Pyrimidine derivatives (compounds 1-7) and quinazoline derivatives (compounds 8-33) were screened against a panel of SK-Hep-1 cell lines (a hepatocellular carcinoma (HCC) cell) for growth-inhibitory activities. MTT assay was used to measure growth inhibition. The compound concentrations causing 50% cell growth inhibition ($IC_{50}$ values) were determined by interpolation from dose-response curves. MTT (3-(4,5-dimethylthiazol-2-yl)-2,5-diphenyl tetrazolium bromide) assay was performed as follow.

The effect of individual test compounds on cell viability was assessed by using the MTT in 6 replicates. Sk-Hep-1 cells were seeded and incubated in 96-well, flat-bottomed plates for 24 hours, and were exposed to various concentrations of test compounds dissolved in DMSO (final concentration, 0.1%) for 48 hours. Controls received DMSO vehicle at a concentration equal to that in drug-treated cells. The medium was removed, replaced by 200 µL of 0.5 mg/mL MTT in 10% fetal bovine serum containing DMEM (Dulbecco's Modified Eagle Medium), and cells were incubated in the carbon dioxide incubator at 37° C. for 2 hours. Supernatants were removed from the wells and the reduced MTT dye was solubilized in 100 µL/well DMSO. Absorbance at 570 nm was determined on a plate reader.

The result of MTT assay showed that $IC_{50}$ values of compounds 6, 8, 13, 18-23, and 25-33 were smaller than 10 µM. Especially, compounds 31 had the smallest $IC_{50}$ value (1.95 µM) among these compounds. Next, $IC_{50}$ values of compounds 7, 9, 10, 14, 17, and 24 were within 10-20 µM. As for compounds 1-5, 11, 12, 15, 16, the $IC_{50}$ values were all greater than 40 µM.

For compounds 8 and 9, the $IC_{50}$ values were very close (7.5±0.5 v. 12.3±0.6). Compound 9 was synthesized by methylation of the substituted phenyl amine group at the position 4 of the quinazoline. This implies that hydrogen donor ability of the substituted phenyl amine group is not necessary for the induction of cell death. In addition, as methylation at the substituted phenyl amine group is known to dramatically reduce the binding ability of quinazoline with EGFR, compound 9 further provides a proof that induction of cell death of quinazoline derivatives is independent of EGFR inhibition.

For compounds 11 and 15, a hydroxyl group was introduced into the phenyl ring. The $IC_{50}$ greater than 40 µM shows that no activity against SK-Hep1 cells. This suggests that hydrophobic interaction is required in this area.

For compounds 14 and 16, a phenyloxy group and a 4-cyano-phenyloxy was introduced into the phenyl ring. Compound 14 exhibited higher activity than compound 16 (15.3±0.6 µM v. >40 µM). This reveals that an electron-withdrawing group on the benzene ring is not favored for inducing cell death.

For the mono-substituted quinazoline derivatives (Embodiment 3), compound 8 exhibited the most potent growth inhibitory activity (7.5±0.5 µM). Interestingly, when the quinazoline skeleton of the mono-substituted quinazoline derivatives was simplified to the pyrimidine skeleton (Embodiment 1), no inhibitions were detected in cell growth assays. However, the compounds 6 and 7 with phenylamine di-substituents at positions 2, 4 in pyrimidine (Embodiment 2) showed more potent anti-tumor activity than the mono-substituted pyrimidine derivatives (Embodiment 1) in cell growth assays. This result suggests that a phenylamine group connected to position 2 of pyrimidine plays a crucial role in cancer-cell growth inhibitory activity.

Accordingly, a second substituted phenyl amine group was further introduced at the position 2 of the quinazoline (Embodiment 4). These derivatives showed more potent activity than mono-substituted derivatives against HCC cells. This result suggests that the second substituted phenyl amine group at the position 2 of the quinazoline plays a significant role in the cancer-cell growth inhibitory activity.

In compounds 18-33, compounds 19, 22, 27, 28, 31 and 33 exhibited higher potency with low $IC_{50}$ values (2.8, 2.8, 2.60, 2.55, 1.95 and 2.65 µM, respectively) against HCC cells whereas compound 24 only showed moderate activity (14.5 µM), indicating that substitutions with hydrophobic properties, such as phenyloxy (compound 19) and benzyl groups (compound 22) exhibited higher CIP2A inhibitory activity than the hydrophilic cyanophenyl groups (compound 24). In addition, compound 23 showed much better inhibition than compound 24 (3.9 µM v. 14.5 µM), suggesting that the connection position of cyanophenyl group to phenyl ring plays an important role in CIP2A inhibition.

Next, compounds 19, and 34-36 were screened against a panel of Hep3B cell lines for growth-inhibitory activities. The result of MTT assay showed that $IC_{50}$ values of compounds 19, and 34-36 were 1.28, 3.35, 3.27 and 3.38 µM, respectively. Compounds 87-90, 95 and 96 were screened against a panel of PLC5 cell lines for growth-inhibitory activities. The result of MTT assay showed that $IC_{50}$ values of compounds 87-90, 95 and 96 were 8.2, 12.74, 20.2, 0.77, 0.95 and 0.61 µM.

Validation of the Action Mode of Pyrimidine and Quinazoline Derivatives

Inhibition of CIP2A Expression

Quinazoline derivatives have previously been evaluated as EGFR inhibitors. However, the quinazoline derivatives above had very low potency against EGFR because of the second substituted group at the position 2 of the quinazoline. However, the quinazoline derivatives above were found to be capable of repressing oncoprotein CIP2A expression and induced cell death as shown above. Therefore, it was hypothesized that quinazoline derivatives downregulate CIP2A and p-Akt, and consequently enhance cell apoptosis.

Figure 2:
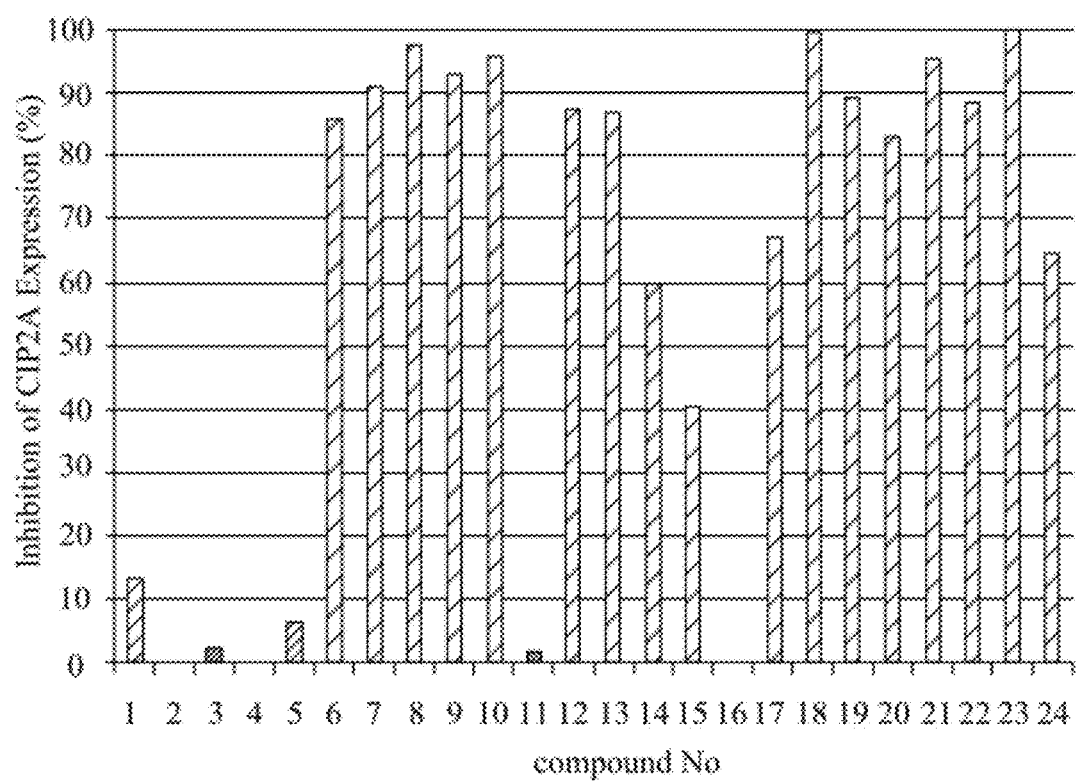
FIG. 2 is the inhibition (%) of CIP2A expression by compounds 1-24 at a concentration of 20 μM for 24 hours in SK-Hep1 cells (hepatocellular carcinoma cell).

Accordingly, the pyrimidine and quinazoline derivatives above were screened by using western blot analysis for expression of CIP2A in SK-Hep1 cells. Before the western blot analysis, the SK-Hep-1 cells were maintained in DMEM supplemented with 10% FBS, 100 units/mL penicillin G, 100 µg/mL streptomycin sulfate and 25 µg/mL amphotericin B in a 37° C. humidified incubator in an atmosphere of 5% $CO_2$ in air. In this western blot analysis, SK-Hep1 cells were respectively treated with compounds 1-24 at a concentration of 20 µM for 24 hours. The results of inhibition effect on CIP2A expression are shown in FIG. 2. In FIG. 2, the mono-substituted pyrimidine derivatives (compounds 1-5) have no appreciable change in CIP2A expression. Di-substituted pyrimidine (compounds 6-7) and quinazoline compounds (compounds 8-24) on the other hand showed a high degree of repression of CIP2A.

Figure 8:
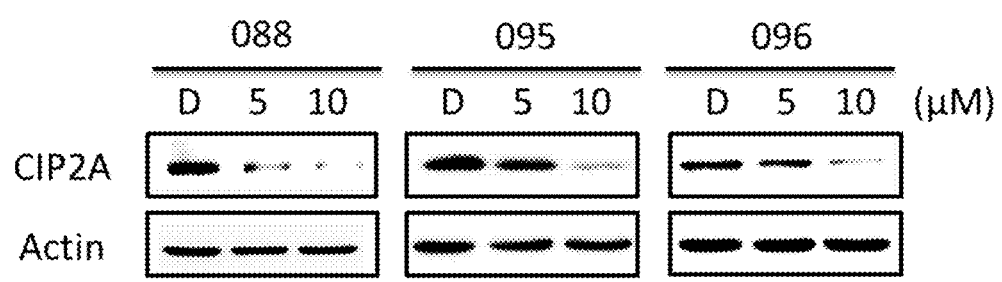
FIG. 8 is the inhibition of CIP2A expression by compounds 88, 95 and 96 in PLC/PRF/5 cells for 48 hours (1% FBS).

PLC/PRF/5 cells were exposed to compounds 88, 95 and 96 at various doses (5 and 10 µM) for 48 hours. Total lysates were subjected to CIP2A protein analysis by western blot. Actin was used as a loading control. The results of inhibition effect on CIP2A expression in a dose-dependent manner are shown in FIG. 8. In FIG. 8, compounds 88, 95 and 96 showed a high degree of repression of CIP2A at the concentration of 10 µM.

Quantitative Polymerase Chain Reaction (qPCR) Assay

In addition, a quantitative polymerase chain reaction (qPCR) assay was used to find the correlation coefficient ($R^2$) between the $IC_{50}$ of CIP2A inhibition and the $IC_{50}$ of cell growth. The correlation coefficient ($R^2$) between the $IC_{50}$ of CIP2A inhibition and the $IC_{50}$ of cell growth was found to be 0.9519. This indicates that the decreased level of CIP2A induced by these derivatives is well correlated with cell toxicity.

The qPCR was performed as follow. Total RNA was isolated from SK-Hep1 cell line with TRIzol (Invitrogen). An aliquot of 2.5 µg/12.1 µL of total RNA was used as the template in the synthesis of first-strand cDNA using an oligo (dT) primer and the AMV reverse transcriptase system (Roche Diagnostics) by Thermal Cycler (RTC-200, MJ Research). The method of qPCR was followed according to the method described by Ponchel et al (Ponchel, F. et al. *BMC Biotechnol* 2003, 3, 18). qPCR was performed using a Roche Light Cycler 480 sequence detection system (Roche Applied Science,). Thermocycling was performed in a final volume of 20 µl containing 2.5 µl of cDNA sample, 200 nM of each of the primers, and 6.5 µL of SYBR Green I master mix (Roche).

The relative differences in expression levels between genes were expressed using cycle time (Ct) values as follows: the Ct value of the gene of CIP2A was first normalized to that for GAPDH in the same sample, then the difference between the treatment and control group was calculated and expressed as an increase or decrease in cycle numbers compared with the control. Oligonucleotide sequences were as follows: CIP2A, 5'-TGG CAA GAT TGA CCT GGG ATT TGG A-3'(sense) and 5'-AGG AGT AAT CAA ACG TGG GTC CTG A-3' (antisense); GAPDH, 5'-CGA CCA CTT TGT CAA GCT CA-3'(sense) and 5'-AGG GGT CTA CAT GGC AAC TG-3' (antisense). The following PCR conditions were used: denaturation at 95° C. for 10 min followed by 40 cycles of 94° C. for 1 min, annealing for 1 min at 60° C., and elongation for 1 min at 72° C., and a final elongation step at 72° C. for 10 min.

Correlation of Down-Regulating CIP2A and P-Akt With EGFR Phosphorylation

Figure 3A:
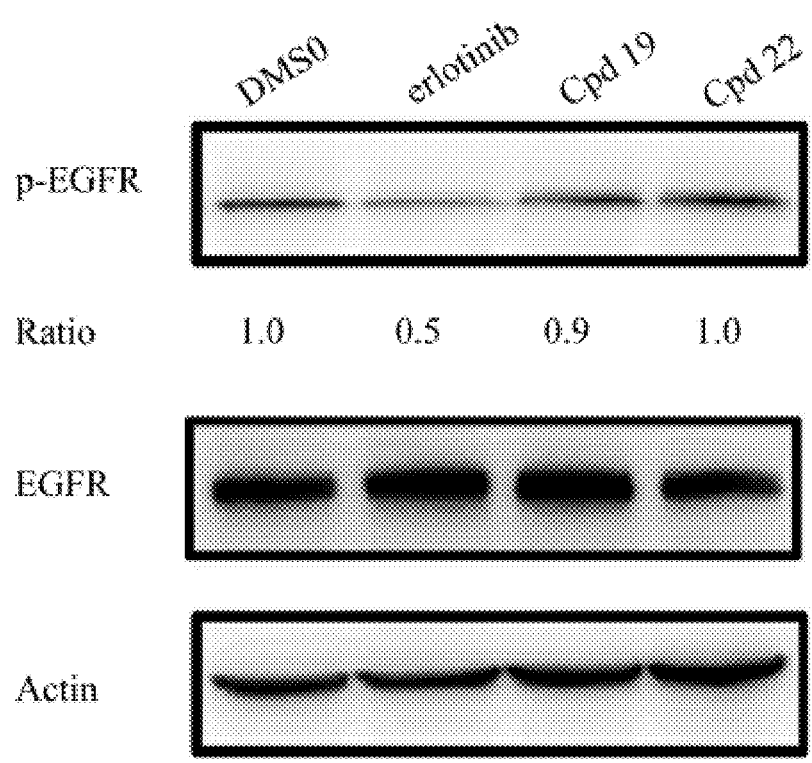
FIG. 3A is the western blot analysis of inhibiting EGFR phosphorylation activity by erlotinib, compound 19, and compound 22 in PC9 cells, respectively.

Next, the most potent compounds 19 and 22 were used to study whether down-regulation CIP2A and p-Akt is correlated to EGFR phosphorylation. FIG. 3A is the western blot analysis of inhibiting EGFR phosphorylation activity by erlotinib, compound 19, and compound 22, respectively. In FIG. 3A, PC9 cells (a human lung adenocarcinoma) were treated with erlotinib, compound 19, and compound 22 at 2 µM for 24 h. The result of FIG. 3A shows that compound 19 and 22 have no inhibitory effect on EGFR kinase. This data confirms that the second substituted-quinazoline derivatives significantly reduce the binding affinity to ATP bind domain of EGFR kinase.

Figure 3B:
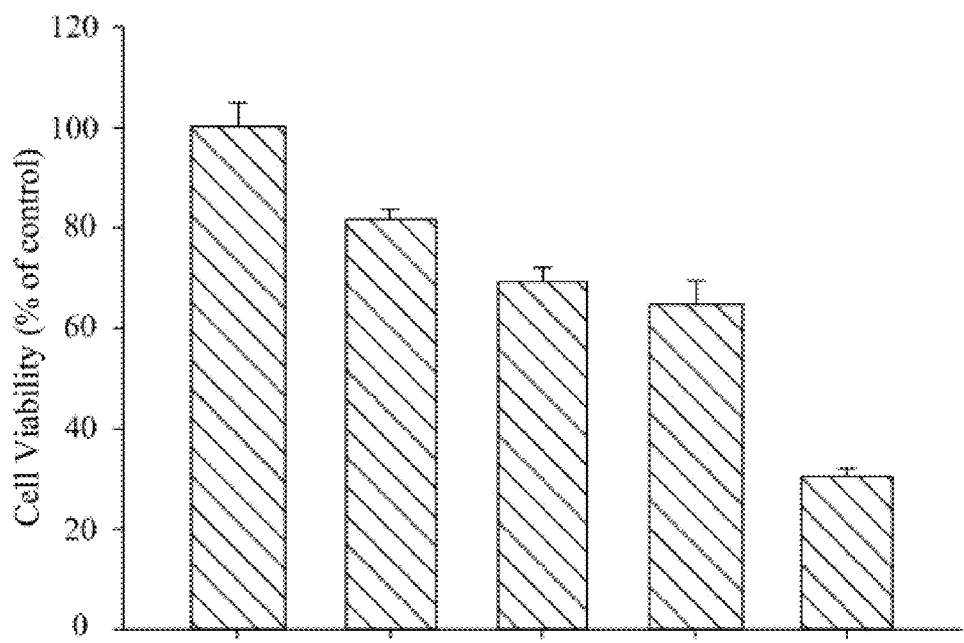
FIG. 3B is the cell viability (upper part) and CIP2A expressions (lower part) in response to compound 19 or erlotinib treatment in SK-Hep1 cell.
Figure 3B:
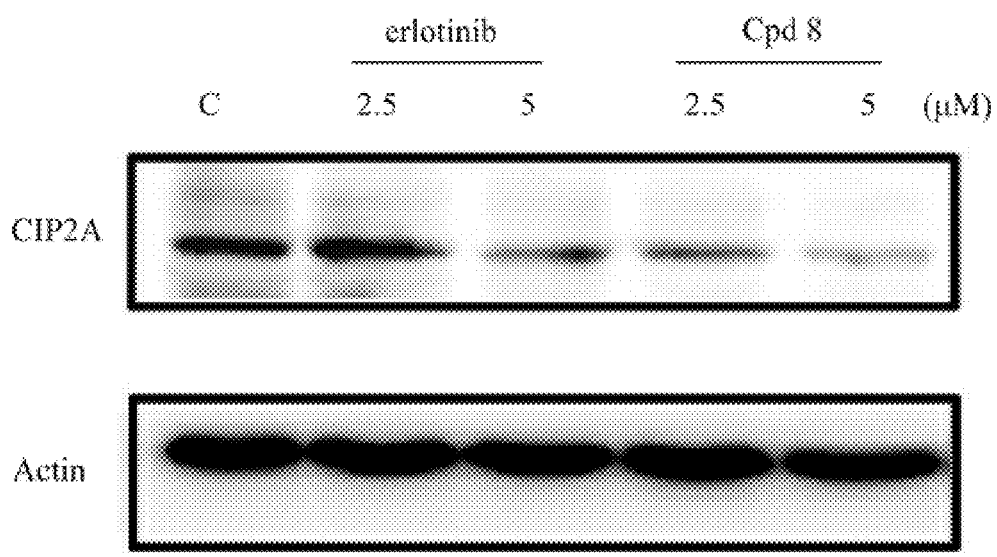

Cell viability, measured by MTT assay, and CIP2A expressions, analyzed by western blot, in response to compound 19 or erlotinib treatment in SK-Hep1 cell line were analyzed. SK-Hep-1 cells were treated with erlotinib and compound 19 at 2.5 and 5 µM for 24 h, respectively. The SK-Hep1 cells were then analyzed with western blot assay and MTT assay. The results are shown in FIG. 3B. In FIG. 3B, compound 19 can reduce the CIP2A expression and the cell viability in a dosage dependent manner, and was more potent than erlotinib. These results suggest that CIP2A plays an important role in regulating cell viability.

Similarly, CIP2A expressions analyzed by western blot were also performed for lung cancer cells, H358, H460, and H322 cell lines. Moreover, drug-induced apoptotic cell death was also assessed by western blot analysis of activated caspases cleaved poly(ADP-ribose)polymerase (PARP). The cleavage of PARP is explained as follow. The compound induces apoptotic signal which cleave the procaspase 3 to the active caspase 3. The activation of caspase 3 further cleaves PARP and inactivate PAPR function. The events are thought to be required in late apoptosis. Therefore, the PARP cleavage is an indicator of apoptosis.

Figure 3C:
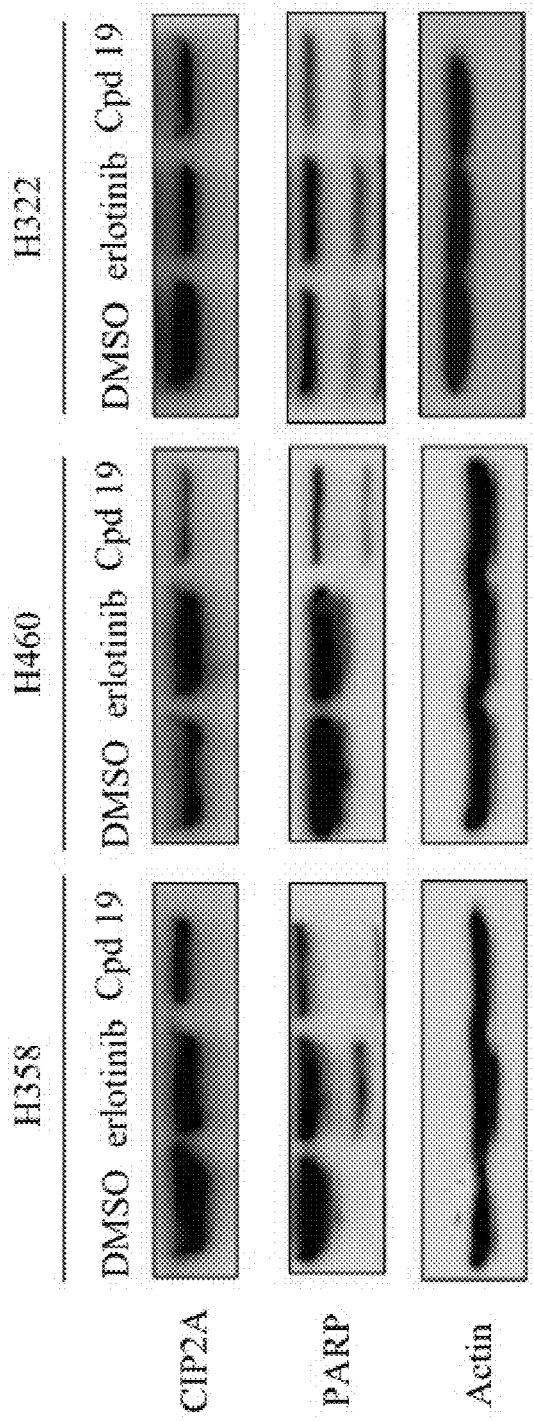
FIG. 3C is the CIP2A expressions and PARP cleavage in response to compound 19 or erlotinib treatment at a concentration of 5 μM in H358, H460, and H322 cells (lung cancer cells).

The results are shown in FIG. 3C. The result of FIG. 3C shows that compound 19 can down-regulate the expression of CIP2A and induce the cleavage of PARP in all of the H358, H460, and H322 cell lines. In the PARP row of FIG. 3C, the upper bands represented the uncleavage PARP, and the middle band and lower band represented cleavage PARP.

Correlation Between Down-regulating CIP2A and Suppressing p-Akt

Figure 4A:
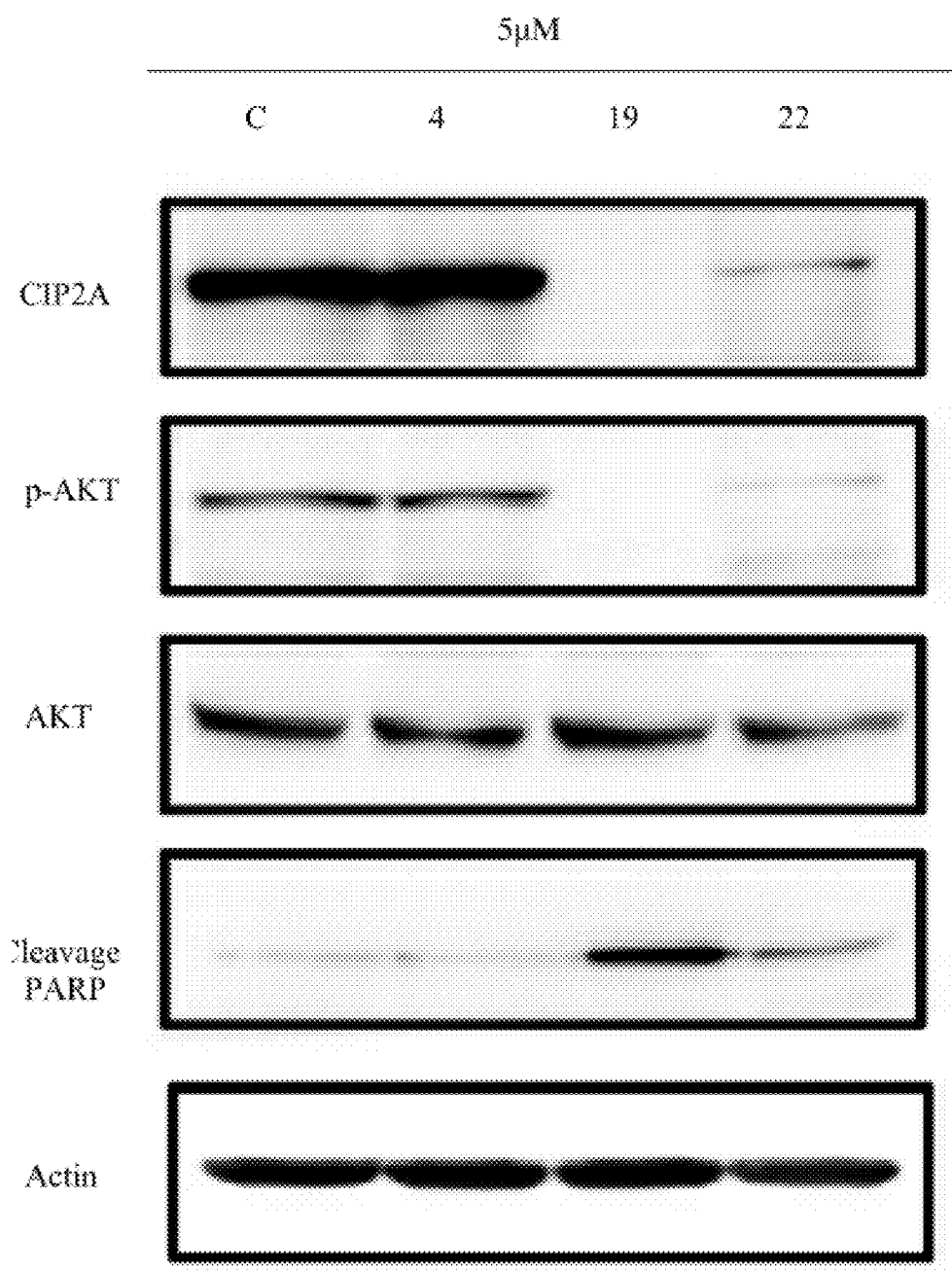
FIG. 4A is the western blot analysis of the effect of the compounds 4, 19, and 22 on phosphorylation of Akt, PARP and Actin in SK-Hep-1 cells.

Next, compounds 11, 19, and 22 were used to explore whether downregulation of CIP2A lead to suppression of p-Akt. FIG. 4A is the western blot analysis of the effect of the compounds 4, 19, and 22 on phosphorylation of Akt, PARP and Actin. In this western blot analysis, SK-Hep-1 cells were respectively treated with compounds 4, 19, and 22 at a concentration of 5 µM for 30 hours. In FIG. 4A, compounds 19 and 22 showed the activity of inhibiting CIP2A expression, reducing p-Akt level, and inducing PARP cleavage. That is, compound 19 and 22 can substantially increase apoptotic cell death to inhibit cancer growth. However, compound 4 showed no activity of inhibiting CIP2A expression, reducing p-Akt level, and inducing PARP cleavage.

Figure 4B:
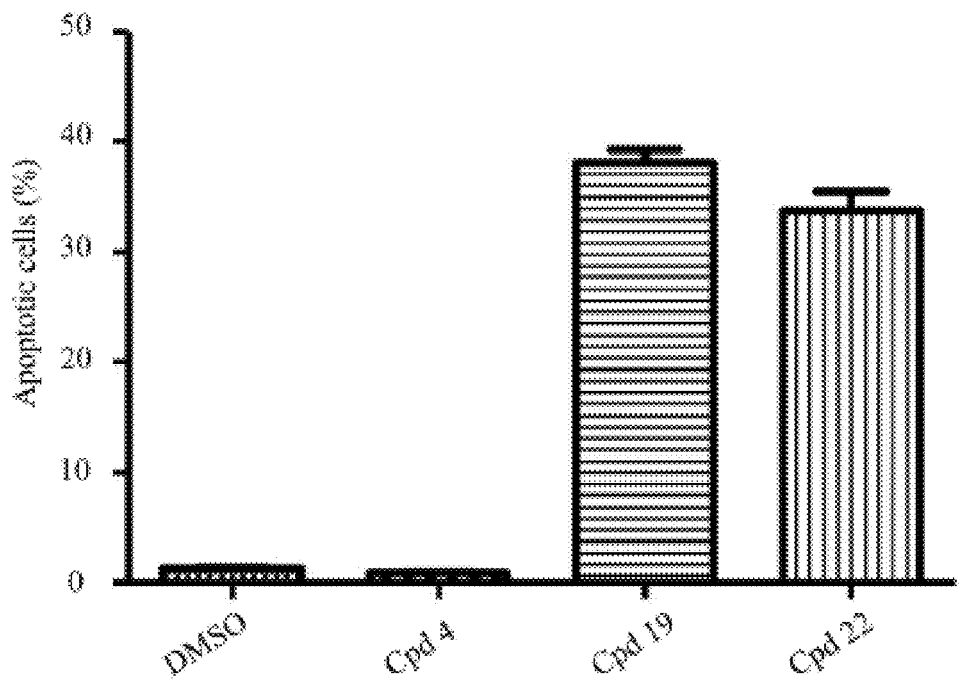
FIG. 4B is flow cytometry analysis of cell death induced by compounds 4, 19, and 22 at 5 μM, after 24 h of treatment in SK-Hep-1 cells. Columns, mean (n=3); bars, SD; *$P<0.05$
Figure 4C:
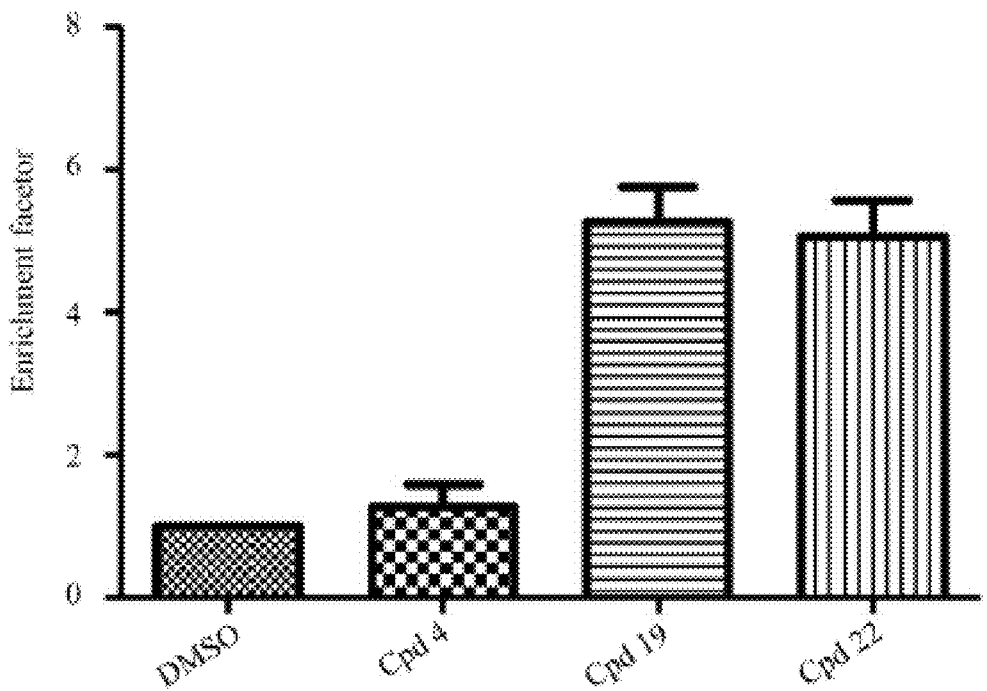
FIG. 4C is ELISA analysis of cell death to analyze effects of compounds 4, 19, and 22 on DNA fragmentation in SK-Hep-1 cells. Columns, mean (n=3); bars, SD; *P<0.05

FIG. 4B is flow cytometry analysis of cell death induced by compounds 4, 19, and 22 at 5 µM, after 24 h of treatment in SK-Hep-1 cells. The apoptotic cells were assessed by flow cytometry (sub-G1). After Sk-Hep-1 cells were treated with compounds 4, 19, and 22, Sk-Hep-1 cells were trypsinized, collected by centrifugation and resuspended in PBS. After centrifugation, the cells were washed in PBS and resuspended in potassium iodide (PI) staining solution. Specimens were incubated in the dark for 30 min at 37° C. and then analyzed with an EPICS Profile II flow cytometer (Coulter Corp., Hialeah, Fla.). All experiments were performed in triplicate FIG. 4C is ELISA analysis of cell death to analyze effects of compounds 4, 19, and 22 on DNA fragmentation in SK-Hep-1 cells. The effect of compounds 4, 19 and 22 on cell viability was assessed by a cell death detection ELISA kit (Roche Applied Science, Mannheim, Germany). SK-Hep-1 cells were treated with compounds 4 and 19 at 22 at 2.5 and 5 µM for 24 h. The cells were collected and assayed according to the standard protocol provided by the manufacturer.

The results of FIGS. 4B-4C show that compounds 19 and 22 induced cell apoptosis. These results are consistent with their inhibition of CIP2A expression.

CIP2A Knockdown Experiment (in Supplementary Material)

In order to know whether CIP2A is a key regulator of cell survival, we have used genetic knockdown CIP2A and then determine the cell survival with colongenic assay.

Figure 5A:
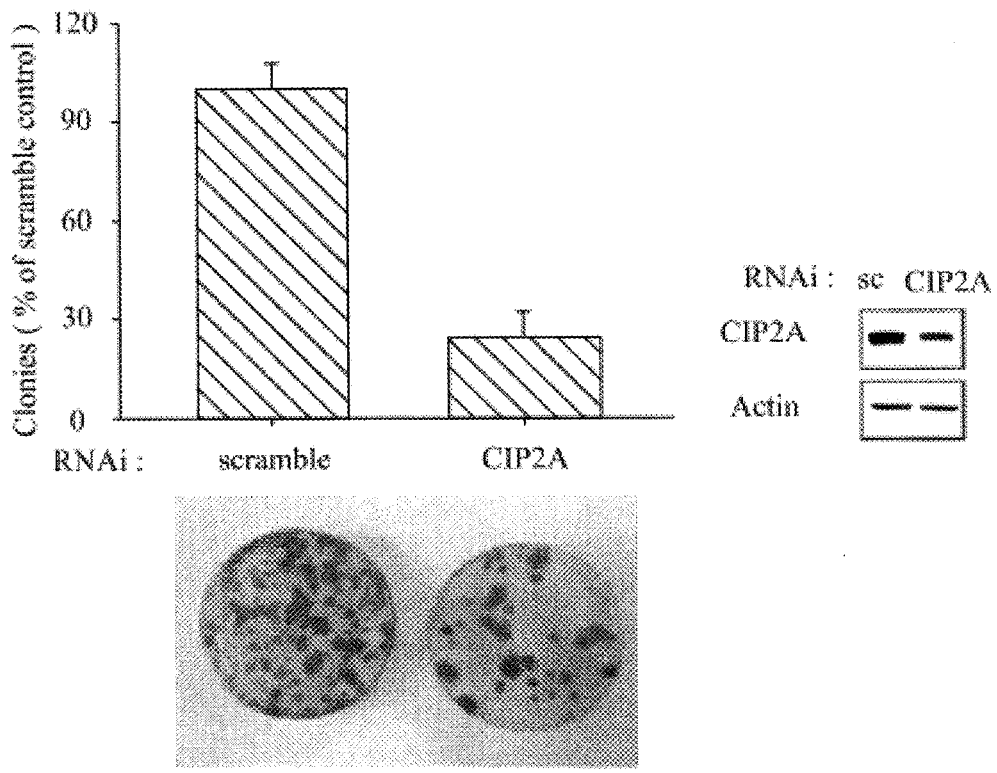
FIG. 5A shows the effect of CIP2A knowicjdiwn in clonogenic assay.

For colony formation, SK-Hep1 cells transfected with scramble siRNA or CIP2A-specific siRNA for 48 hours were seeded in triplicate onto 6 cm plates (10,000 cells per plate). After 7 days of culturing, cells were stained with crystal violet, and colonies containing more than 50 cells were counted. The obtained results are shown in FIG. 5A.

Figure 5B:
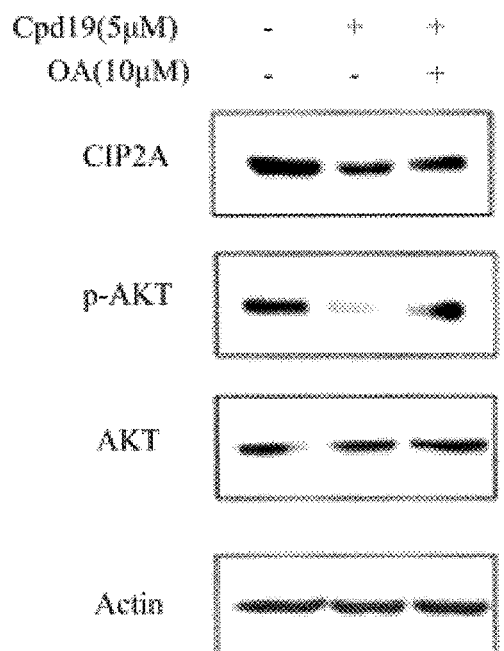
FIG. 5B shows the effect of okadaic acid in compound 19 induced CIP2A inhibition.

The effect of okadaic acid (OA) in compound 19 induced CIP2A inhibition is shown in FIG. 5B. In FIG. 5B, it can be seen that okadaic acid, a phosphatase inhibitor, reversed p-Akt level in compound 19 treated SK-Hep-1 cells, indicating that compound 19 inhibit CIP2A, activate PP2A and further dephosphorelate p-Akt. In other words, in the present of okadaic acid, the activation of PP2A by compound 19-incuced CIP2A inactivation is blocked.

Animal Test

In vivo efficacy was determined in nude mice with PLC5 and Huh-7 xenografts.

Xenograft Tumor Growth

Male NCr athymic nude mice (5-7 weeks of age) were obtained from the National Laboratory Animal Center (Taipei, Taiwan). The mice were housed in groups and maintained under standard laboratory conditions on a 12-hour light-dark cycle. They were given access to sterilized food and water ad libitum. All experimental procedures using these mice were performed in accordance with protocols approved by the Institutional Laboratory Animal Care and Use Committee of National Taiwan University. Each mouse was inoculated s.c. in the dorsal flank with $1\times10^6$ HCC cells suspended in 0.1 ml of serum-free medium containing 50% Matrigel (BD Biosciences, Bedford, Mass.). When tumors reached 150-200 mm³, mice received erlotinib at 50 mg/kg/day or compounds 8 and 19 at 20 mg/kg/day daily by oral gavage for 3 weeks. Controls received vehicle.

Statistical Analysis

Tumor growth data points are reported as mean tumor volume±SE. Comparisons of mean values were performed using the independent samples t test in SPSS for Windows 11.5 software (SPSS, Inc., Chicago, Ill.).

Cell Culture of PLC5 and Huh-7 HCC Cell Lines (HCC Cell Lines)

PLC5 HCC cell line was obtained from American Type Culture Collection (ATCC; Manassas, Va.). The Huh-7 HCC cell line was obtained from the Health Science Research Resources Bank (HSRRB; Osaka, Japan; JCRB0403).

All cells were immediately expanded and frozen down such that all cell lines could be restarted every 3 months from a frozen vial of the same batch of cells. No further authentication was conducted in our lab. Cells were maintained in DMEM supplemented with 10% FBS, 100 units/mL penicillin G, 100 µg/mL streptomycin sulfate, and 25 µg/mL amphotericin B in a 37° C. humidified incubator and an atmosphere of 5% $CO_2$ in air. Lysates of HCC cells treated with drugs at the indicated concentrations for various periods of time were prepared for immunoblotting of PARP, P-Akt, Akt, etc.

In Vivo Effects of Erlotinib and Compounds 8 and 19 on HCC Xenograft Tumors

The in vivo effects of erlotinib, compound 8, and compound 19 on HCC xenograft tumors were analyzed. Tumor-bearing mice were treated with vehicle, erlotinib (50 mg/kg/day), compound 8 (20 mg/kg/day), or compound 19 (20 mg/kg/day) p.o. daily for 3 weeks. All animals tolerated the treatments well without observable signs of toxicity and had stable body weights throughout the course of study. No gross pathologic abnormalities were noted at necropsy.

The results of xengraft study above were listed in Table below. The data listed in the Table below were the data after 21 days of treatment.

|  | Erlotinib (inhibition) | Cpd 8 (inhibition) | Cpd 19 (inhibition) |
| --- | --- | --- | --- |
| PLC5 cell | 50.0% | 45.7% | 60.6% |
| Huh7 cell | 8.8% | 40.3% | 34.8% |

Figure 6A:
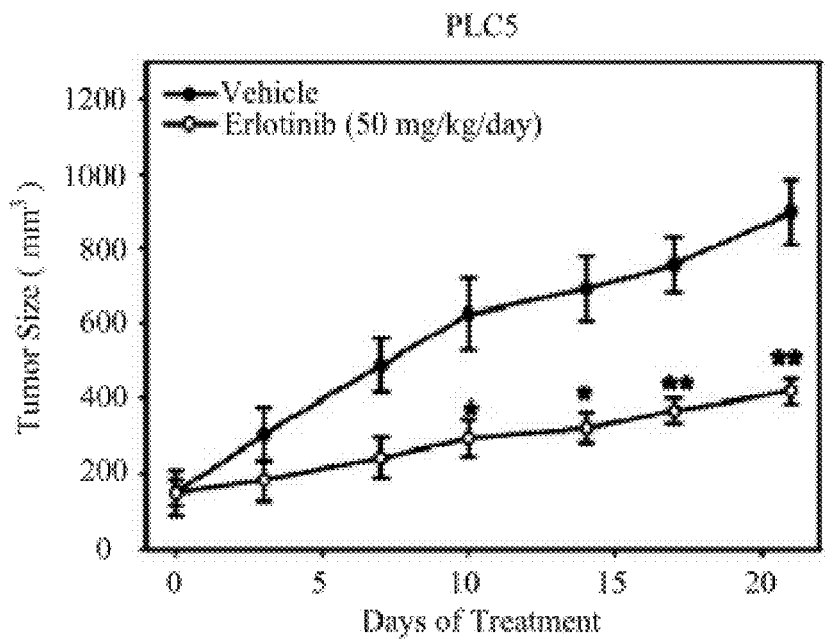
FIGS. 6A and 6B shows the tumor size changed with days of treatment by erlotinib, compound 1, and compound 9 in PLC5 xenograft tumor.
Figure 6B:
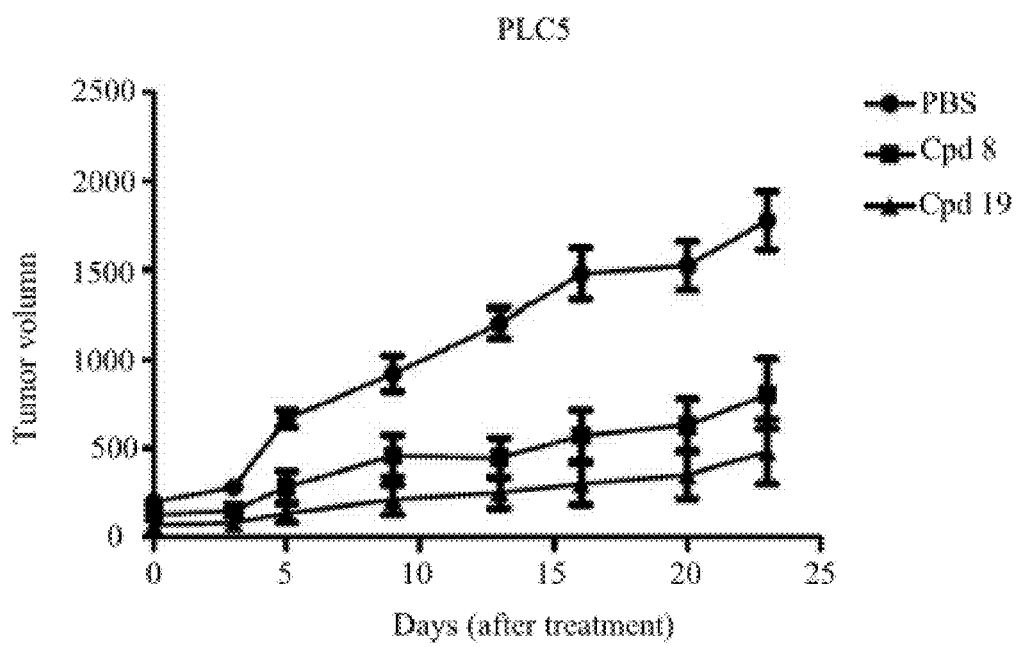

FIGS. 6A and 6B shows the tumor size changed with days of treatment by erlotinib, compound 8, and compound 19 in PLC5 xenograft tumor. The result of FIG. 5B shows that compounds 8 and 19 can significantly reduced the growth of tumor in sensitive PLC5 tumors. Especially, compound 19 even shown better inhibitory effect on PLC5 tumors than erlotinib (FIG. 5A).

Figure 7A:
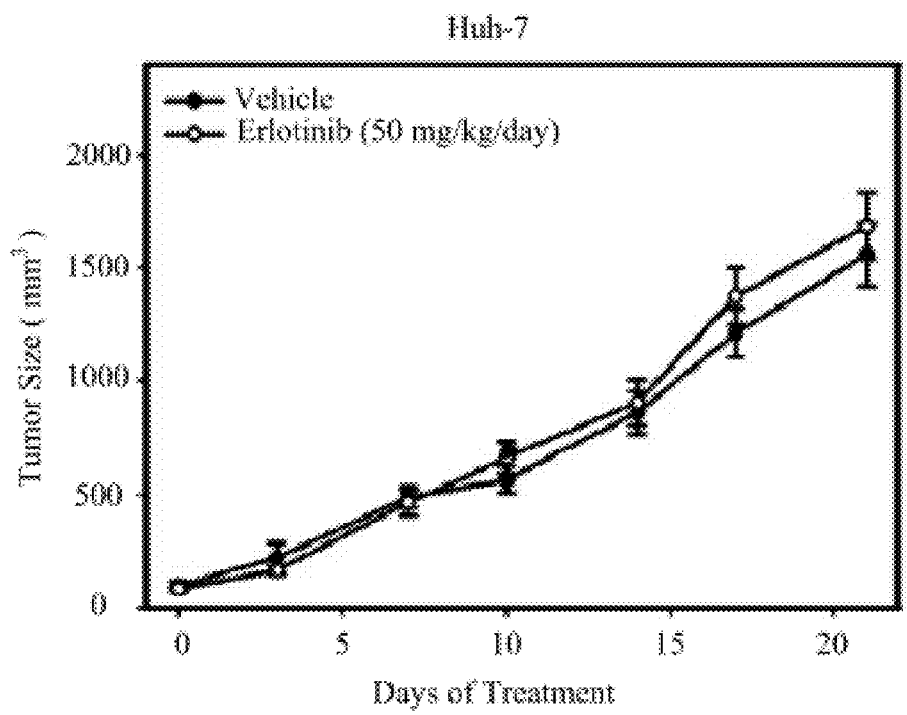
FIGS. 7A and 7B shows the tumor size changed with days of treatment by erlotinib, compound 1, and compound 9 in Huh-7 xenograft tumor.
Figure 7B:
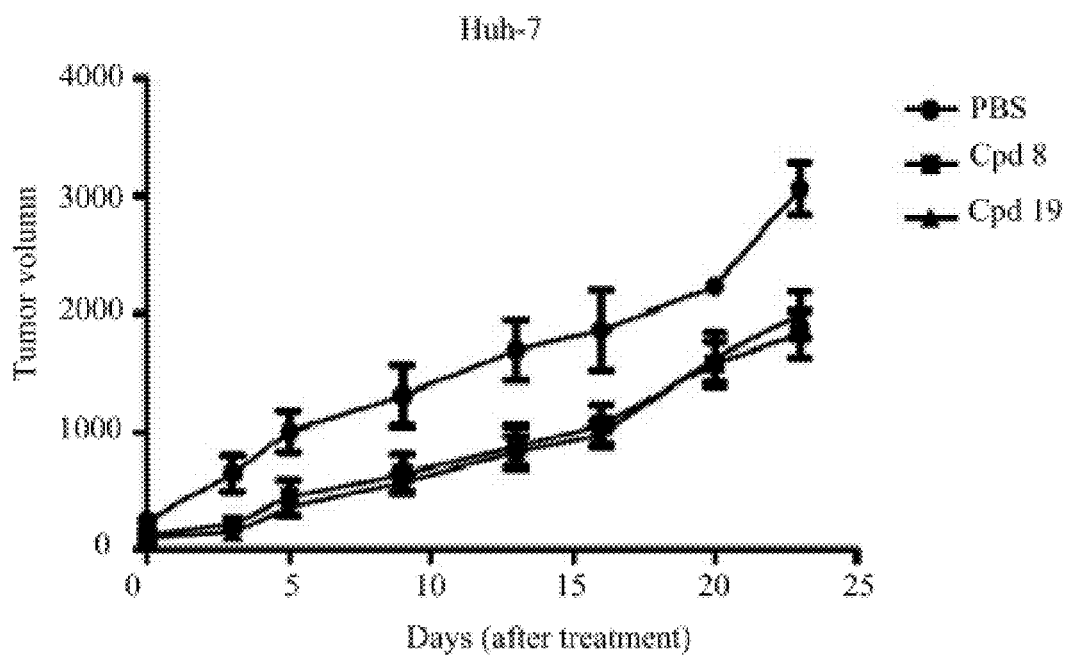

FIGS. 7A and 7B shows the tumor size changed with days of treatment by erlotinib, compound 8, and compound 19 in Huh-7 xenograft tumor. The result of FIG. 6A shows that erlotinib treatment had no effect on tumor growth in resistant Huh-7 cells. However, the result of FIG. 6B shows that compounds 8 and 19 still possess better inhibitory effect on Huh-7 tumors than erlotinib.

In light of foregoing, a series of pyrimidine and quinazoline-derived compounds were synthesized and their cytotoxicity was explored with interesting SAR results. Structural modifications indicated that di-phenylamine derivatives with quinazoline and pyrimidine skeletons are required for activity.

According to MTT assay, most of these derivatives had micromolar level potency against SK-Hep-1 cells. Compounds 19 and 22 showed the most potent inhibition of CIP2A expression and cell survival activity, whereas compound 4 had no activity in either assay. Furthermore, compounds 19 and 22 reduced Akt phosphorylation after repressing CIP2A, whereas compound 4 had no activity against p-Akt and CIP2A.

These results suggest selective sensitivity in response to the different substituted functional groups in quinazoline. Moreover inhibition of CIP2A expression correlated with cytotoxicity in SK-Hep-1 cells upon drug treatment. Testing of compounds 19 and 22 in an in vivo HCC model shows that compounds 19 and 22 are capable of significantly reducing the growth of tumor in sensitive PLC5 tumors.

All the features disclosed in this specification (including any accompanying claims, abstract, and drawings) may be replaced by alternative features serving the same, equivalent or similar purpose, unless expressly stated otherwise. Thus, each feature disclosed is one example only of a generic series of equivalent or similar features.

What is claimed is:
1. An aryl amine substituted pyrimidine having a chemical structure (IV) below:
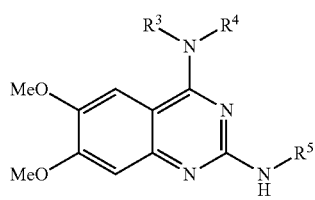
wherein $R^3$ is
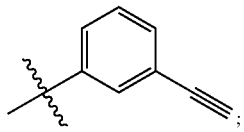 [SMILES: *c1cccc(C#C)c1]
$R^4$ is H, an aliphatic group with carbon number of 1-5, an amino-substituted aliphatic group, or a benzyl group; and
$R^5$ is
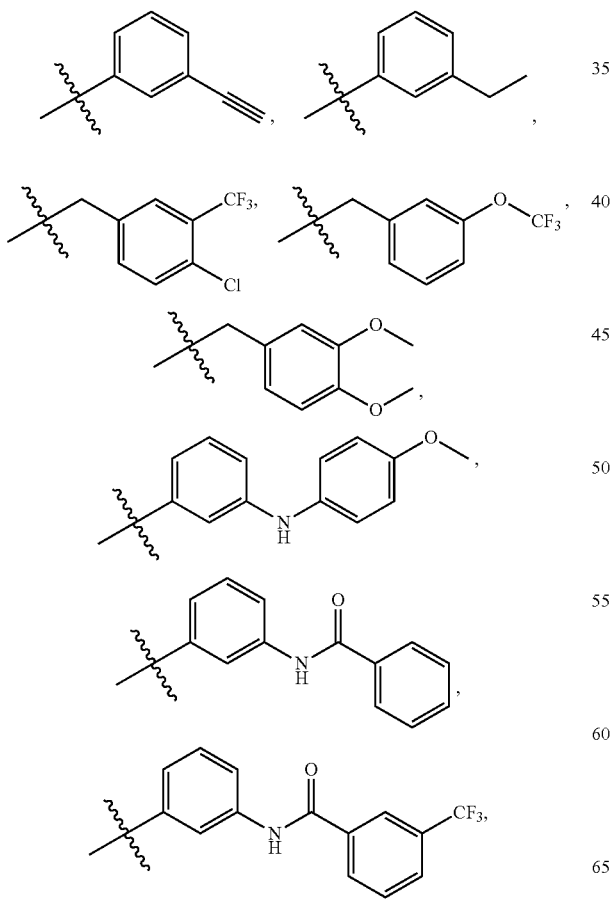
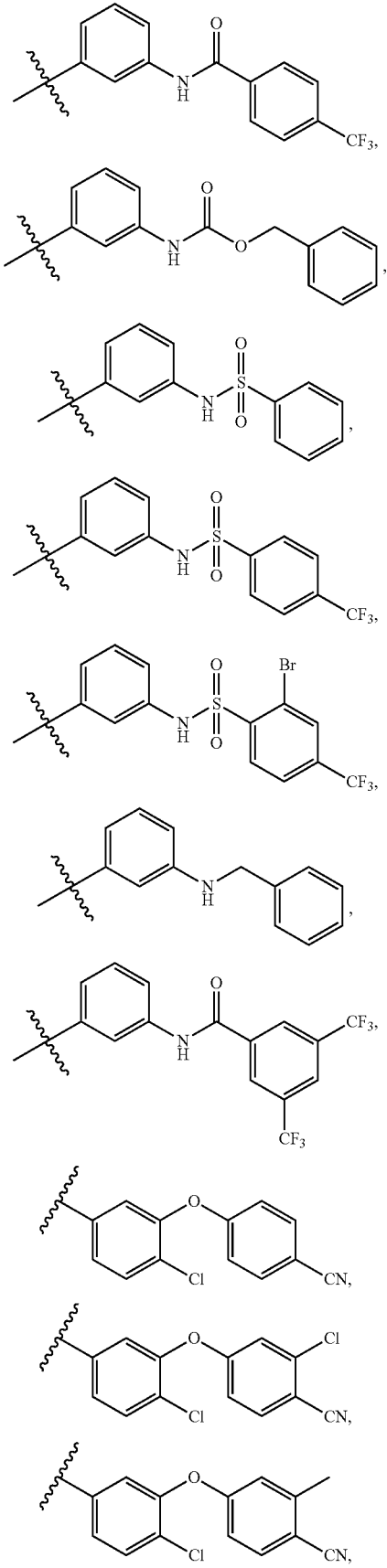

2. The aryl amine substituted quinazoline of claim 1, wherein the $R^4$ is H, 3. The aryl amine substituted quinazoline of claim 1, wherein the aryl amine substituted quinazoline having a chemical structure (VII) below:
   wherein the $R^5$ is (VII)

4. The aryl amine substituted quinazoline of claim 1, wherein the aryl amine substituted quinazoline having a chemical structure (VII) below:

wherein the R⁵ is

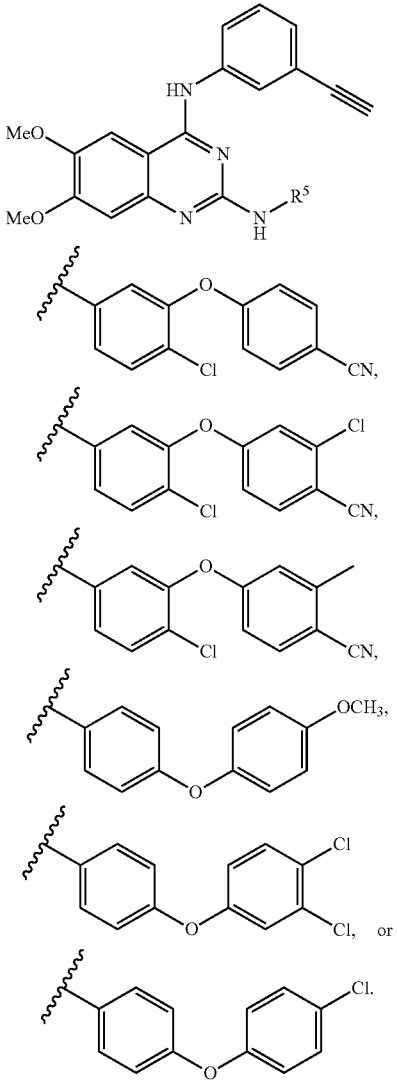

5. The aryl amine substituted quinazoline of claim 1, wherein the chemical structure (IV) is at least one of the following:
- N²,N⁴-Bis(3-ethynylphenyl)-6,7-dimethoxyquinazoline-2,4-diamine;
- N²-(3-ethylphenyl)-N⁴-(3-ethynylphenyl)-6,7-dimethoxy quinazoline-2,4-diamine;
- N²-(4-Chloro-3-(trifluoromethyl)benzyl)-N⁴-(3-ethynylphenyl)-6,7-dimethoxyquinazoline-2,4-diamine;
- N⁴(3-Ethynylphenyl)-6,7-dimethoxy-N²-(3-(trifluoromethoxy)benzyl)quinazoline-2,4-diamine;
- N²-(3,4-dimethoxybenzyl)-N⁴-(3-ethynylphenyl)-6,7-dimethoxyquinazoline-2,4-diamine;
- N-(3-(4-(3-ethynylphenylamino)-6,7-dimethoxyquinazolin-2-ylamino)phenyl)benzenesulfonamide;
- N-(3-(4-(3-Ethynylphenylamino)-6,7-dimethoxyquinazolin-2-ylamino)phenyl)-3-(trifluoromethyl)benzenesulfonamide;
- 2-Bromo-N-(3-(4-(3-ethynylphenylamino)-6,7-dimethoxyquinazolin-2-ylamino)phenyl)-4-(trifluoromethyl)benzenesulfonamide;
- N-(3-(4-(3-ethynylphenylamino)-6,7-dimethoxyquinazolin-2-ylamino) phenyl)benzamide;
- N²-(3-(benzylamino)phenyl)-N⁴-(3-ethynylphenyl)-6,7-dimethoxyquinazoline-2,4-diamine;
- N-(3-(4-(3-ethynylphenylamino)-6,7-dimethoxyquinazolin-2-ylamino)phenyl)-3,5-bis(trifluoromethyl)benzamide;
- N-(3-(4-(3-ethynylphenylamino)-6,7-dimethoxyquinazolin-2-ylamino)phenyl)-3-(trifluoromethyl)benzamide;
- 4-(2-chloro-5-((4-((3-ethynylphenyl)amino)-6,7-dimethoxyquinazolin-2-yl)amino)phenoxy)benzonitrile;
- 2-chloro-4-(2-chloro-5-((4-((3-ethynylphenyl)amino)-6,7-dimethoxyquinazolin-2-yl)amino)phenoxy)benzonitrile;
- 4-(2-chloro-5-((4-((3-ethynylphenyl)amino)-6,7-dimethoxyquinazolin-2-yl)amino)phenoxy)-2-methylbenzonitrile;
- N²-(4-(3,4-dichlorophenoxy)phenyl)-N⁴-(3-ethynylphenyl)-6,7-dimethoxyquinazoline-2,4-diamine;
- N²-(4-(3,4-dichlorophenoxy)phenyl)-N⁴-(3-ethynylphenyl)-6,7-dimethoxyquinazoline-2,4-diamine;
- N²-(4-(4-chlorophenoxy)phenyl)-N⁴-(3-ethynylphenyl)-6,7-dimethoxyquinazoline-2,4-diamine.

6. A pharmaceutical composition comprising an effective amount of a compound of claim 1 and a pharmaceutically acceptable carrier.

7. The pharmaceutical composition of claim 6, wherein the composition is capable of inhibiting the expression of cancerous inhibitor of protein phosphatase 2A (abbreviated as CIP2A).

8. The pharmaceutical composition of claim 6, wherein the compound having a chemical structure (VII) below:

wherein the R⁵ is

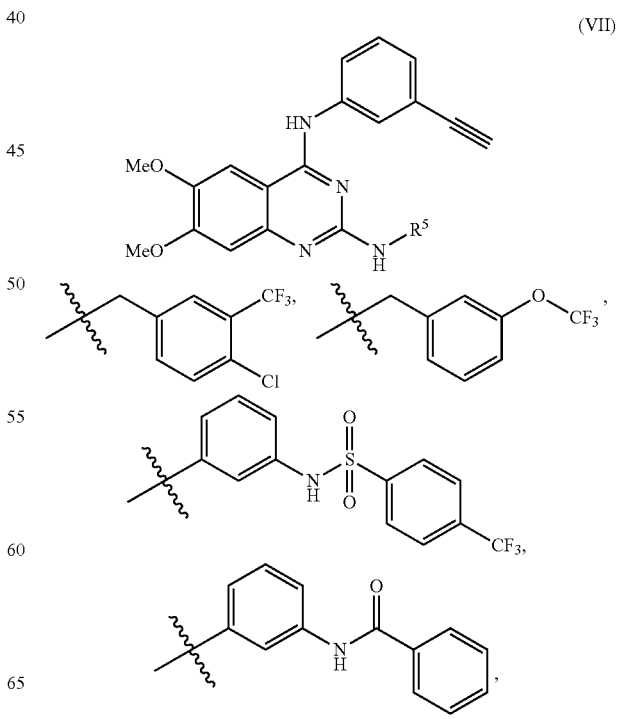

-continued

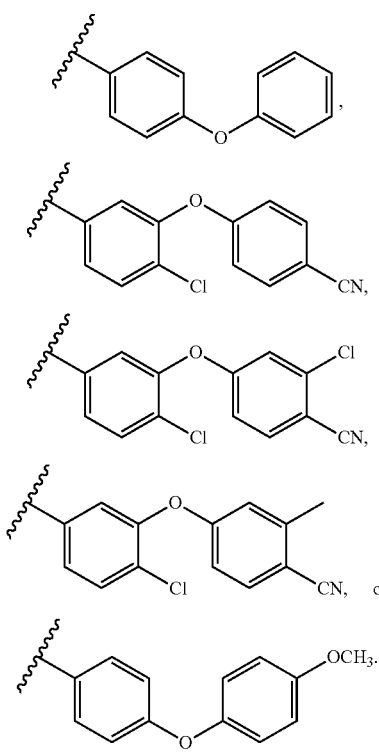

9. A method of inhibiting the expression of CIP2A comprising contacting a cell with an effective amount of a compound of claim 1.

10. The method of claim 9, wherein the compound having a chemical structure (VII) below:

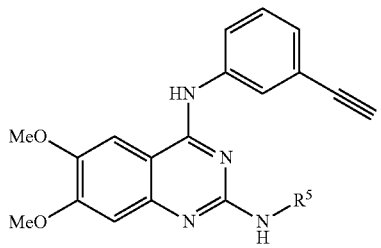

(VII)

wherein the $R^5$ is

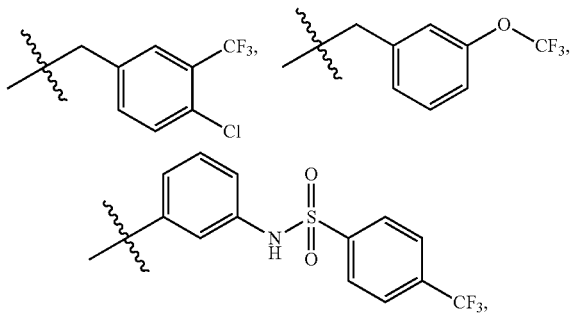

-continued

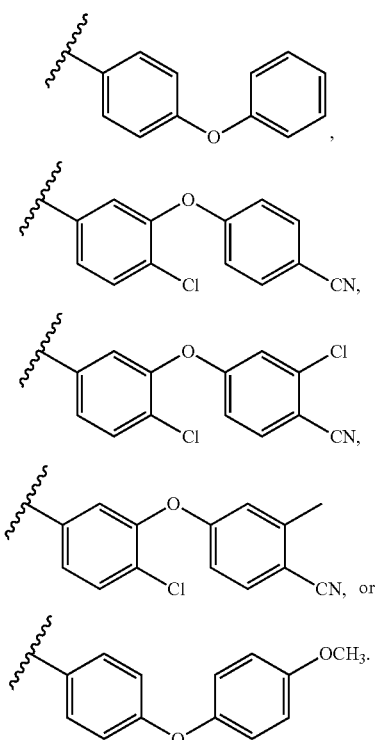

11. A method of treating a cancer comprising administrating an effective amount of a compound of claim 1 by a needed subject.

12. The method of claim 11, wherein the compound having a chemical structure (VII) below:

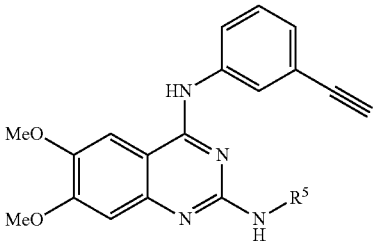

(VII)

wherein the $R^5$ is

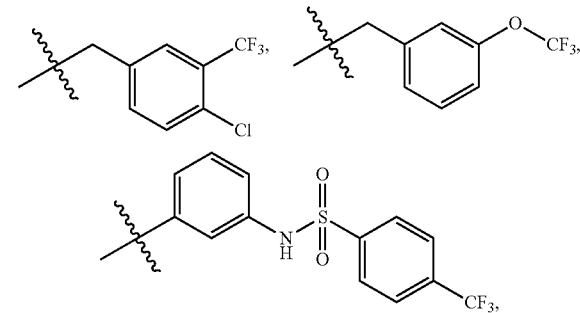

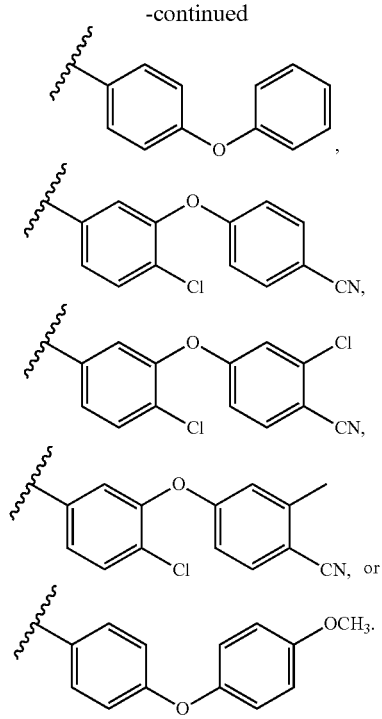
13. The method of claim 11, wherein the cancer is a hepatocellular carcinoma or a lung cancer.
* * * * *

SEQUENCE LISTING

```
<160> NUMBER OF SEQ ID NOS: 4

<210> SEQ ID NO 1
<211> LENGTH: 25
<212> TYPE: DNA
<213> ORGANISM: Artificial sequence
<220> FEATURE:
<223> OTHER INFORMATION: Synthetic Oligonucleotide

<400> SEQUENCE: 1 tgg caa gat tga cct ggg att tgg a                               25

<210> SEQ ID NO 2
<211> LENGTH: 25
<212> TYPE: DNA
<213> ORGANISM: Artificial sequence
<220> FEATURE:
<223> OTHER INFORMATION: Synthetic Oligonucleotide

<400> SEQUENCE: 2 agg agt aat caa acg tgg gtc ctg a                               25

<210> SEQ ID NO 3
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 3 cga cca ctt tgt caa gct ca                                      20

<210> SEQ ID NO 4
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 4 agg ggt cta cat ggc aac tg                                      20
```